(12) United States Patent
Cheung et al.

(10) Patent No.: US 6,310,247 B1
(45) Date of Patent: Oct. 30, 2001

(54) 7-ARYL-6(Z)-HEPTATRIENOIC ACID RETINAMIDES

(75) Inventors: Adrian Wai-Hing Cheung, Glen Rock; Stephen B. Ferguson; Louise Helen Foley, both of Clifton; Allen John Lovey, North Caldwell, all of NJ (US)

(73) Assignee: Hoffmann-LA Roche Inc., Nutley, NJ (US)

( * ) Notice: Subject to any disclaimer, the term of this patent is extended or adjusted under 35 U.S.C. 154(b) by 0 days.

(21) Appl. No.: 09/460,911

(22) Filed: Dec. 14, 1999

Related U.S. Application Data

(60) Provisional application No. 60/112,635, filed on Dec. 17, 1998.

(51) Int. Cl.[7] ............... C07C 233/04; C07C 233/09; A61K 31/165
(52) U.S. Cl. ............ 564/180; 564/170; 564/174; 554/35; 514/617; 514/622
(58) Field of Search .................. 564/170, 174, 564/182; 554/35; 514/617, 622

(56) References Cited

U.S. PATENT DOCUMENTS

| | | |
|---|---|---|
| 5,399,757 | 3/1995 | Maryanoff . |
| 5,705,167 | 1/1998 | Bernardon et al. . |
| 5,721,103 * | 2/1998 | Boehm et al. ............ 435/7.1 |

FOREIGN PATENT DOCUMENTS

| | | |
|---|---|---|
| 0 679 628 A | 11/1995 | (EP) . |
| 95 03274 | 2/1995 | (WO) . |
| WO 96/20913 | 7/1996 | (WO) . |

OTHER PUBLICATIONS

Retinoids in Oncology, Marcel Dekker, Inc. Publisher, Eds. W.K. Hong & R. Lotan; Chapter 14, Retinoids & Breast Cancer By A. Costa, pp. 301–322, 1993.
Retinoids Press Publishers; Eds. M.B. Sporn, A.B. Roberts, D.S. Goodman, Chapter 15, pp. 606–607, 1994.
A.N. Fanjul et al., JBC 271, pp. 22441–22446 (1996).
A. Dipietrantonio, et al. BBRC 224, pp. 837–842 (1996).
M. Ponzoni et al. Cancer Res. vol. 55, pp. 853–861, 1995.
J.A. Fontana, et al. Can. Res. 50, 1997–2002, 1990.
B. Van der Burg, B. et al. Mol. Cell Endocrinol 91, pp. 149–157 (1993).
T.T.Y. Wang, et al. Cancer Lett. vol. 107, pp. 65–71 (1996).
M.S. Sheikh, et al. Cancer Res. vol. 53, pp. 6036–6041 (1993).
C.P. Zhou, et al. Clin. Cancer Res. vol. 4, pp. 1345–1355 (1998).
R.L. Scher et al., Otolaryngol Head Neck Surg vol. 118, pp. 464–471 (1998).
K. Dowlatshahi, et al. Cancer Lett. vol. 47, pp. 187–192 (1989).
R.C. Moon et al. Cancer Res. vol. 39, pp. 1339–1346 (1979).
A. Costa et al., Cancer Res. vol. 54, pp. 2032S–2037S (1994).
L.N. Chan et al. Anticancer Res. vol. 17, pp. 499–504 (1997).
D. Vorländer et al, Berichte Der Deutsche Chemischen Gesellschaft, vol. 62, (1929) pp. 545–549 (XP002133650).
Sheikh et al, Carcinogenesis, vol. 16, 10, (1995) pp. 2477–2486.

* cited by examiner

*Primary Examiner*—Shailendra Kumar
(74) *Attorney, Agent, or Firm*—George W. Johnston; Patricia S. Rocha-Tramaloni; Robert A. Silverman

(57) ABSTRACT

Novel trienoic retinoid compounds of

Formula 1

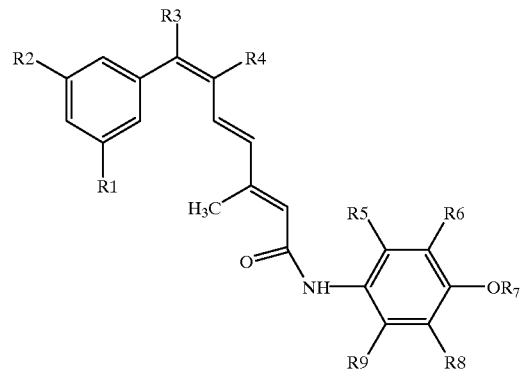

with apoptotic activity useful for the prevention and treatment of cancer.

32 Claims, No Drawings

7-ARYL-6(Z)-HEPTATRIENOIC ACID RETINAMIDES

This application claims priority under 35 U.S.C. §119(e) of provisional application(s) Serial No. 60/112,635, filed Dec. 17, 1998.

BACKGROUND OF THE INVENTION

Retinoic acids (RA)s modulate the growth and differentiation of normal and malignant cells in vitro and in vivo and have been extensively studied for their potential use as therapeutic and preventative agents of a variety of malignancies. All-trans RA and 13-cis RA, which function through the nuclear retinoic acid receptors (RAR) α, β and γ, are known to cause differentiation of certain tumor cells in vitro. 9-cis RA and its analogs, which bind to a group of receptors known as the retinoic acid X α, β and γ receptors (RXR), as well as to the RAR α, β and γ receptors, have been shown to cause tumor regression. The ability of all-trans RA and 13-cis RA to induce apoptosis has been shown to be very limited, however, the 4-hydroxyphenyl amide of all-trans RA (4-HPR) has been shown to inhibit tumor formation and tumor growth via apoptosis [JBC 271, 22441 (1996) A. N. Fanjul et al; BBRC 224, 837 (1996) A. Dipietrantonio, etal; Cancer Res. 55, 853 (1995) M. Ponzoni, etal].

Apoptosis, or programmed cell death, is one of the most common forms of eukaryotic cell death and is characterized by loss of contact with neighboring cells, chromatin condensation, membrane blebbing, condensation of cytoplasm, and activation of an endogenous endonuclease which generates the characteristic DNA fragments (one of the benchmarks of cellular apoptosis), and finally generation of apoptotic bodies that are phagocytosed by other cells. Apoptosis is a normal process and is involved in building, sculpting and maintaining tissues during development and throughout life. Apoptosis is also an important defense mechanism against viral infection and the emergence of cancer. The development of cancer appears to involve both excess cell proliferation and the resistance to normal apoptosis stimuli. A number of tumor promoters have been shown to induce resistance to apoptosis [FASEB Journal 8, 864 (1994) S. C. Wright, etal]

While retinoic acids have been found to be effective in treating carcinomas, many retinoic acids and other retinoid compounds are very toxic, producing deleterious adverse effects such as hypervitaminosis A which limit their use in the prevention and treatment of cancer. In treating breast cancer the situation is further complicated by cancer cells which are capable of changing their sensitivity to compounds used in treatment. Cells which are initially positive for estrogen receptor (ER+) can become negative for estrogen receptor (ER−) following anti-estrogen therapies. The retinoic acids and retinoids, like most chemotherapeutic agents, are active only against ER+breast carcinoma cells and not active against estrogen receptor negative ER—breast carcinoma cells. [Can Res 50, 1997 (1990) J. A. Fontana, et al; Mol Cell Endocrinol 91, 149 (1993) B. Van der Burg, et al] Thus compounds which show activity against both ER− and ER+ breast carcinoma cells are very important for treatment of breast cancer.

A preliminary measure for possible antitumor/anticancer therapeutic activity is the induction of apoptosis, or programmed cell death, in immortalized carcinoma cells. A number of existing chemotherapeutic agents (e.g. 5FU, Adriamycin, Taxol), as well as radiation therapy, induce apoptosis in human carcinoma cells in vitro[Cancer 79, 12 (1997) K. Sugamura, etal; Cancer Lett. 93, 147 (1995) S. M. Tu, et al; Ann NY Acad. Sci 784, 550 (1996) R. M. Gangemi, etal]. Another measure of antitumor or anticancer activity is the inhibition of cell growth, or cell cycle arrest, which prevents cells from dividing, though not necessarily killing the cells. It has been shown that a specific retinoic acid amide, all trans 4-hydroxyphenyl retinamide (4-HPR), is capable of inhibiting cell growth and inducing apoptosis in both ER+ and ER− breast carcinoma cells. [Cancer Lett. 107, 65 (1996) T. T. Y. Wang, et al].

This compound is also known to inhibit cell growth and to induce apoptosis in many other tumor cell types including lung carcinoma cell and hematopoetic malignancies. 4-HPR is effective in inducing apoptosis in cells that are resistant to retinoids that activate RARs efficiently.[Carcinogenesis 16, 2477 (1995) M. S. Sheikh, etal; Cancer Res. 53, 6036 (1993) D. Delia, etal] 4-HPR is capable of tumor regression in vivo [Clin. Cancer Res. 4, 1345 (1998) C. P. Zou, etal; Otolaryngol Head Neck Surg 118, 464 (1998) R. L. Scher, etal; Cancer Lett 47, 187 (1989) K. Dowlatshahi, etal], and acts as a potent chemopreventative agent against a number of malignancies [Cancer Res. 39, 1339 (1979) R. C. Moon, etal; Cancer Res. 54, 2032S (1994) A. Costa, etal; Anticancer Res. 17, 499 (1997) L. N. Chan, etal]. In vitro, 4-HPR appears to induce apoptosis and cause inhibition of cell growth in both ER+ and ER− breast carcinoma cell lines. The major toxicity seen in the clinic with 4-HPR was night vision impairment.

Aromatic 6-cis trienoic acids have been reported to induce apoptosis in carcinoma cells and were reported to have low toxicity (WO96/20913). However, it has been determined that one such compound is inactive against ER− and ER+ carcinoma cells in that it does not induce apoptosis ((2E, 4E,6Z)-7-[3,5-bis(trifluoromethyl)phenyl-3,7-dimethyl-2,4, 6-heptatrienoic acid). Therefore, such compounds would seem to be of little interest.

Surprisingly, the 7-aryl-6-cis heptatrienoic acid retinamides of this invention are effective against both ER+ and ER− breast carcinoma cells in vitro, reduce the number of tumors in the NMU rat tumor model, and do not exhibit the toxic or adverse effects generally associated with retinoids.

SUMMARY OF THE INVENTION

The invention comprises compounds of the formula

Formula 1

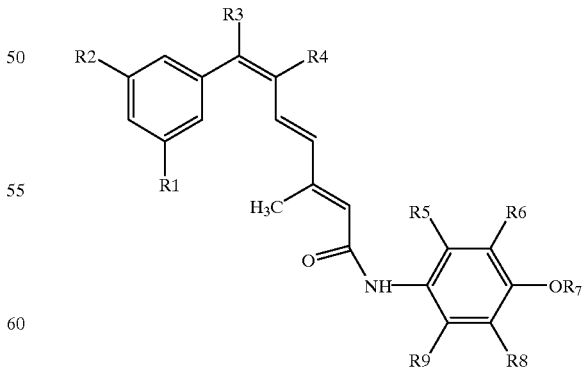

wherein $R^1$ and $R^2$ are independently hydrogen, halogen, alkyl, alkoxy, or trihalomethyl; $R^3$ is hydrogen or alkyl; and $R^4$ is hydrogen except when $R^3$ is alkyl then $R^4$ may be alkyl; $R^5$, $R^6$, and $R^8$ and $R^9$ are independently halogen, hydrogen, hydroxy, alkyl, or alkyloxy; and $R^7$ is hydrogen alkyl; which are free of 6-trans isomers.

These 6Z (e.g. 7-aryl-6-cis) heptatrienoic acid retinamide compounds are effective in inducing apoptosis in premalignant and malignant cells. The compounds inhibit the proliferation of cells derived from cancerous solid tumors, especially non-small-cell lung carcinoma, rectal carcinoma, and breast carcinoma, thus are useful for the treatment of cancer forming solid tumors, especially non-small-cell lung carcinoma, colorectal carcinoma and breast carcinoma.

The compounds described herein are particularly effective at inducing apoptosis in ER– breast carcinoma cells as well as ER+ cells. Furthermore, the 6-cis retinamide compounds of this invention are effective in inducing apoptosis in carcinoma cells that were once ER+ and have become ER–. Finally, these compounds are effective at dosage levels low enough to avoid deleterious or toxic side effects.

DETAILED DESCRIPTION OF THE INVENTION

The invention comprises compounds of the formula

Formula 1

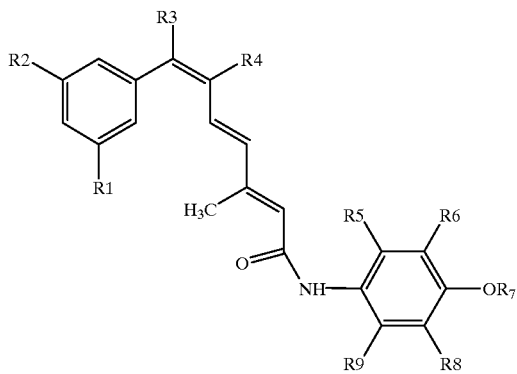

wherein $R^1$ and $R^2$ are independently hydrogen, halogen, alkyl, alkoxy, or trihalomethyl; $R^3$ is hydrogen or alkyl; and $R^4$ is H except when $R^3$ is alkyl then $R^4$ may be alkyl; $R^5$, $R^6$, and $R^8$ and $R^9$ are independently halogen, hydrogen, hydroxy, alkyl, or alkyloxy; and $R^7$ is hydrogen or alkyl; which are free of 6-trans isomers.

Although the preferred $R^7$ is hydrogen, in any compound of this invention $R^7$ may be alkyl such as methyl. Similarly, although preferred compounds are those of formula 2 below where the positions occupied by $R^5$, $R^6$, and $R^8$ and $R^9$ in formula 1 are all hydrogen, in any compound of this invention, any one or more of these substituents may be halogen or hydroxy or alkyl or alkoxy, in any combination.

Compounds of particular interest are compounds of formula 2

Formula 2

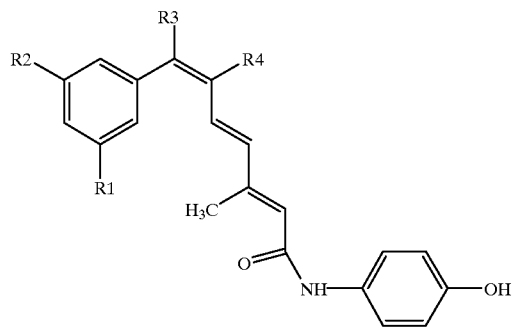

where $R^1$, $R^2$, $R^3$, and $R^4$ are as above.

Other compounds of interest include compounds of formula 1 where $R^3$ is alkyl such as methyl, and $R^4$ is hydrogen, or $R^3$ and $R^4$ are alkyl such as methyl, or $R^3$ and $R^4$ are hydrogen. Also of interest are compounds of formula 1 where $R^1$ and $R^2$ are independently hydrogen, halogen such as bromine, alkyl such as methyl, alkoxy such as methoxy, or trihalomethyl—especially trifluoromethyl. Also part of this invention are compounds of formula 2 where $R^3$ is alkyl such as methyl, and $R^4$ is hydrogen, or $R^3$ and $R^4$ are alkyl such as methyl, or $R^3$ and $R^4$ are hydrogen, and compounds of formula 2 where $R^1$ and $R^2$ are independently hydrogen, halogen such as bromine, alkyl such as methyl, alkoxy such as methoxy, or trihalomethyl—especially trifluoromethyl.

In any of the compositions of this invention, $R^1$ and $R^2$ may be the same or different. Thus in any compound described below (compounds of formula 1: i, ii, or iii and compounds of formula 2: i, ii, or iii), $R^1$ and $R^2$ are preferably the same, but may also be different. Thus in compounds where $R^1$ and $R^2$ are halogen, they may be the same or different halogens. Similarly $R^1$ and $R^2$ may be the same or different alkyls or alkoxys. In addition $R^1$ and $R^2$ may be members of different groups, i. e. $R^1$ may be a halogen while $R^2$ is an alkyl, or $R^1$ may be an alkyl while $R^2$ is hydrogen, and so on.

Compounds of formula 1 where i) $R^3$ is alkyl such as methyl, and $R^4$ is hydrogen; or ii) $R^3$ and $R^4$ are hydrogen; or iii) $R^3$ and $R^4$ are both alkyl such as methyl, are of interest. In particular such compounds of i, ii, or iii are of interest when $R^1$ and $R^2$ are trifluoromethyl. In other compounds of i, ii, or iii $R^1$ and $R^2$ may also be halogen such as bromine, alkyl such as methyl, alkoxy such as methoxy, or hydrogen. In the more preferred compounds, $R^3$ is alkyl such as methyl, and $R^4$ is hydrogen. Thus for example compounds where $R^3$ is alkyl and $R^4$ is hydrogen, and $R^1$ and $R^2$ are trifluoromethyl, or where $R^3$ and $R^4$ are both hydrogen and $R^1$ and $R^2$ are halogen, or $R^3$ and $R^4$ are hydrogen and $R^1$ and $R^2$ are methoxy, are part of this invention, as well as the other compounds which have the characteristics described in the first section of this paragraph, e.g. which represent a compound of i or ii or iii where $R^1$ and $R^2$ are halogen, alkyl, alkoxy, or hydrogen etc. as described above.

In addition, compounds of formula 2 where i) $R^3$ is alkyl such as methyl, and $R^4$ is hydrogen; or ii) $R^3$ and $R^4$ are hydrogen; or iii) $R^3$ and $R^4$ are both alkyl such as methyl, are of interest. In particular such compounds of i, ii, or iii are of interest when $R^1$ and $R^2$ are trifluoromethyl. In other compounds of i, ii, or iii $R^1$ and $R^2$ may also be halogen such as bromine, alkyl such as methyl, alkoxy such as methoxy, or hydrogen. In the more preferred compounds, $R^3$ is alkyl such as methyl, and $R^4$ is hydrogen. Thus for example compounds where $R^3$ and $R^4$ are hydrogen and $R^1$ and $R^2$ are bromine, or $R^3$ and $R^4$ are alkyl and $R^1$ and $R^2$ are halogen, or $R^3$ is alkyl and $R^4$ is hydrogen and $R^1$ and $R^2$ are methoxy are part of this invention, as well as the other compounds which have the characteristics described in the first section of this paragraph, e.g. which represent a compound of i or ii or iii where $R^1$ and $R^2$ are halogen, alkyl, alkoxy, or hydrogen etc. as described above.

Thus for example compounds of this invention include compounds of formula 2 where $R^3$ is methyl and $R^4$ is hydrogen. In one such compound $R^1$ and $R^2$ are trifluoromethyl. An example of such a compound is N-(4-hydroxyphenyl)-(2E,4E,6Z)-7 -3,5-bis(trifluoromethyl)phenyl]-3,7-dimethyl-2,4,6-heptatrienamide, a particularly preferred compound. In another such compound, $R^1$ and $R^2$ are bromine. An example of such a compound is N-(4-hydroxyphenyl)-(2E,4E,6Z)-7-[3,5-dibromophenyl]-3,7-dimethyl-2,4,6-heptatrienamide. In yet another such compound, $R^1$ and $R^2$ are methyl. An example of such a compound is N-(4-hydroxyphenyl)-(2E,4E,6Z)-7-[3,5-dimethylphenyl]-3,7-dimethyl-2,4,6-heptatrienamide. In another such compound $R^1$ and $R^2$ are methoxy. An example of such a compound is N-(4-hydroxyphenyl)-(2E,4E,6Z)-7-[3,5-dimethoxyphenyl]-3,7-dimethyl-2,4,6-heptatrienamide. In yet another such compound, $R^1$ and $R^2$ are hydrogen. An example of such a compound is N-(4-hydroxyphenyl)-(2E,4E,6Z)-7-[phenyl]-3,7-dimethyl-2,4,6-heptatrienamide.

Also included in this invention are compounds of formula 2 where $R^3$ and $R^4$ are hydrogen. In one such compound $R^1$ and $R^2$ are trifluoromethyl. An example of such a compound is N-(4-hydroxyphenyl)-(2E,4E,6Z)-7-[3,5-bis(trifluoromethyl)phenyl]-3-methyl-2,4,6-heptatrienamide. In another such compound, $R^1$ and $R^2$ are bromine. In yet another such compound, $R^1$ and $R^2$ are methyl. In another such compound $R^1$ and $R^2$ are methoxy. In yet another such compound, $R^1$ and $R^2$ are hydrogen.

Also included in this invention are compounds of formula 2 where $R^3$ and $R^4$ are methyl. In one such compound $R^1$ and $R^2$ are trifluoromethyl. An example of such a compound is N-(4-hydroxyphenyl)-(2E,4E,6Z)-7-[3,5-bis(trifluoromethyl)phenyl]-3,6,7-trimethyl-2,4,6-heptatrienamide. In another such compound, $R^1$ and $R^2$ are bromine. In yet another such compound, $R^1$ and $R^2$ are methyl. In another such compound $R^1$ and $R^2$ are methoxy. In yet another such compound, $R^1$ and $R^2$ are hydrogen.

As used herein, the term "alkyl" means a saturated hydrocarbon group that contains up to 7 carbon atoms. The term "alkoxy" similarly refers to a compound having up to 7 carbon atoms and linked via an oxygen. Alkyl and alkoxy groups can be straight-chain or branched, such as methyl, ethyl, n-propyl, isopropyl, n-butyl, and t-butyl, or methoxy, ethoxy, n-propoxy, isopropoxy, n-butoxy and t-butoxy. Trihalomethyl groups are methyl groups substituted with three halogens, which are preferably the same but may be different. Trifluoromethyl is an example of a trihalomethyl group. The term "halo" means fluoro, chloro, bromo, or iodo, and the term halogen means fluorine, chlorine, bromine, or iodine.

These compounds are effective at inhibiting or preventing the growth of tumors in premalignant and malignant cells and are useful for the treatment of carcinomas forming solid tumors, especially of the colon, prostate, or cervix, non-small-cell lung carcinoma, small-cell lung carcinoma, head and neck carcinoma and breast carcinoma whether the cells involved are ER– or ER+ . These compounds are especially useful in breast, colorectal, and non-small-cell lung carcinoma. The compounds of this invention can be used to treat such tumors, to retard the development of such tumors, and to prevent the increase in number of tumors.

The anticancer therapeutic activity of compounds of this invention may be demonstrated by various standard in vitro assays. Such assays described below and in the examples are known to indicate anticancer activity and are assays for cancer therapeutics. Compounds of this invention have the structure depicted in formula 1, and anticancer activity as determined by any standard assay, especially assays for apoptosis. The compounds are particularly effective to induce apoptosis in carcinoma cells, causing the death of the cell. Thus a compound has the desired activity if the compound causes carcinoma cells to die when the cells are exposed to the compounds. Carcinoma cells for assays (for example breast, lung, colorectal, etc.) are readily obtained from cell depositories such as the American Type Culture Collection (ATCC) or may be isolated by skilled persons from cancer patients. The type of cancer against which the compound is most active is determined by the type of cell used in the assays. For example a compound which affects ER– breast carcinoma cells would be useful to treat breast carcinoma, especially in reverted ER+ cells.

Carcinoma cells, grown in culture, may be incubated with a specific compound and changes in cell viability may be determined for example, by dyes which selectively stain dead cells or by optical density (O.D.) measurement. If more than 10% of cells have died, the compound is active in inducing apoptosis. The compounds may not directly kill the cells (cellular toxicity) but may modulate certain intra- or extracellular events which result in apoptosis. The anticancer activity of the compounds of this invention may also be determined by assays that access the effects of compounds on cell growth and differentiation. Cell growth inhibition may be determined by adding the compound in question to carcinoma cells in culture with dyes or radioactive precursors, and determining by microscopic cell counting, scintillation counting, or O.D. measurement whether the number of cells has increased over the incubation period. If the number of cells has not increased, growth has been inhibited and the compound is regarded as having therapeutic activity. Similarly, the proportion of cells which have become differentiated after addition of a test compound may be determined by known methods (ie. measuring oxidative burst in HL-60 cells, an indicator of differentiation, by NBT). If 10% or more cells have differentiated, then the compound is regarded as having therapeutic activity. Examples of specific assays are provided in Example IIA.

In vivo assays are also useful to demonstrate anticancer activity. Compounds of this invention may act to reduce the size and/or the number of tumors in laboratory animals such as mice in which tumor growth has been induced. The type of tumor indicates the type of cancer against which primary activity is expected. Specific tumors may be induced by perturbing specific tissues with carcinogens, or by injecting specific types of carcinoma cells. Such an assay is provided in Example IIB. The compounds of the present invention show significant prophylactic and therapeutic activity when evaluated against NMU-induced mammary (breast) tumors in rats. Surprisingly the doses and regimens which are effective are free of significant toxicity. The compounds also show efficacy in reducing number of tumors during the course of the experiment (i.e. chemoprevention) at doses and regimens not associated with toxicity. Furthermore, the compounds are therapeutically active, i.e. are able to effect regression of established first primary tumors. The compounds are also preventitive, i.e. able to significantly prevent formation of new tumors. Retinoids having these therapeutic and preventitive activities have not been previously observed in this experimental animal model.

Thus the compounds of the invention are therapeutically active, producing regression or remission of solid tumors, especially those tumors associated with carcinomas such as breast (ER + and especially ER−), lung, and colorectal.

In accordance with the present invention, treatment of cancers is accomplished by administering a compound of the invention systemically to a patient in an amount effective to treat the cancer. In particular, this invention includes a method of treating breast cancer by providing to an individual with breast cancer an amount of a compound of this invention effective to inhibit growth of the cancer, or carcinoma cells. By inhibiting growth of cancer (carcinoma) cells is meant stopping growth, causing apoptosis, or causing differentiation, or otherwise changing the nature of the cell to render it innocuous. The compound may also be administered prophylactically, for example to a person at risk for cancer, or a person who has already undergone effective treatment generally in a lower dosage than for treatment. The amount of compound used is dependent on the type of cancer, the amount and size of the tumors and on the requirements of the patient. In general a daily dosage of about 1 mg/kg to about 500 mg/kg of body weight, preferably about 20 mg/kg to about 100 mg/kg is a helpful basic range, which may be varied by the skilled practitioner depending on the characteristics and requirements of the patient and his condition. The treatment is typically carried out for a period of about three months, but this depends on the patient's condition and the practitioner's judgement. In prophylactic administration, the duration of administration again depends on the patients condition and the practitioner's plan, but will generally continue for a longer period of time than three months. For the treatments given above, the compound of the invention is administered systemically as a composition containing the compound of the invention, and a pharmaceutically acceptable carrier compatible with said compounds. In preparing such composition, any conventional pharmaceutically acceptable carrier can be used. Generally the preferred unit dosage form is tablets or capsules, which can be administered once or twice daily depending upon the weight and size of the patient. The compounds of this invention may be administered as the sole treatment, or may be used in conjunction with other chemical or biochemical treatments or with radiation or surgery.

In accordance with the invention a compound of the invention can be administered in the form of its pharmaceutically acceptable hydrolyzable esters or prodrugs. Any pharmaceutically acceptable hydrolyzable ester can be used in the compositions and methods of this invention. Among the esters are the aromatic esters such as benzoyl, e.g. where R7 si C(O)phenyl, or alkyl esters e.g. where R7 is C(O)alkyl, where alkyl can be methyl, ethyl, n-propyl, n-butyl, and the like.

The pharmaceutical compositions of this invention can be made up in any conventional form including: (a) a solid form for oral or suppository administration such as tablets, capsules, pills, powders, granules, and the like; (b) sterile, typically aqueous solution or suspension form for intravenous or parenteral administration and (c) preparations for topical administration such as solutions, suspensions, ointments, creams, gels, micronized powders, aerosols and the like. The pharmaceutical compositions may be sterilized and/or may contain adjuvants such as preservatives, stabilizers, wetting agents, emulsifiers, salts for varying the osmotic pressure, and/or buffers.

The compounds of the invention are especially useful in pharmaceutically acceptable oral modes. These pharmaceutical compositions contain one or more compounds of the invention or its pharmaceutically acceptable salts and its pharmaceutically acceptable hydrolyzable esters in association with a compatible pharmaceutically acceptable carrier material. Any conventional carrier material can be used. The carrier material can be an organic or inorganic inert carrier material suitable for oral administration. Suitable carriers include water, gelatin! gum arabic, lactose, starch, magnesium stearate, talc, vegetable oils, polyalkylene-glycols, petroleum jelly and the like. Furthermore, the pharmaceutical preparations may contain other pharmaceutically active agents, preferably a retinoid having RARA activity. Additional additives such as flavoring agents, preservatives, stabilizers, emulsifying agents, buffers and the like may be added in accordance with accepted practices of pharmaceutical compounding.

The pharmaceutical preparations can be made up in any conventional oral dosage form including a solid form for oral administration such as tablets, capsules, pills, powders, granules, and the like. A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician.

The compounds of this invention may be prepared by a skilled person free of 6-trans isomers using standard starting materials, reagents, and methods with the guidance provided below and in Example 1

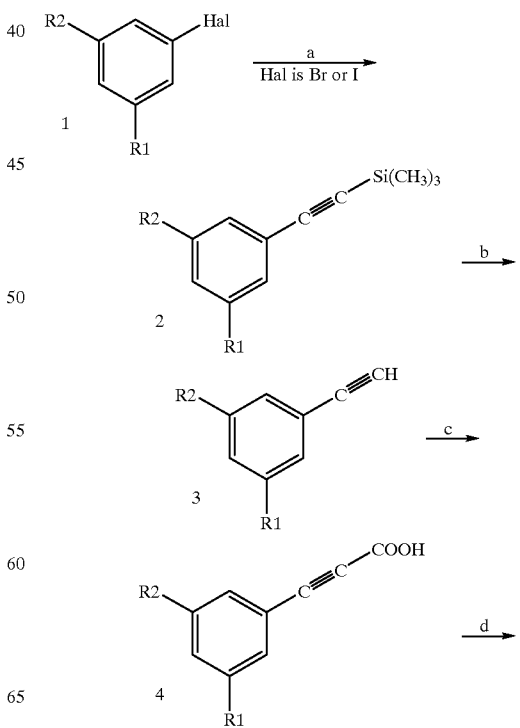

Scheme 1

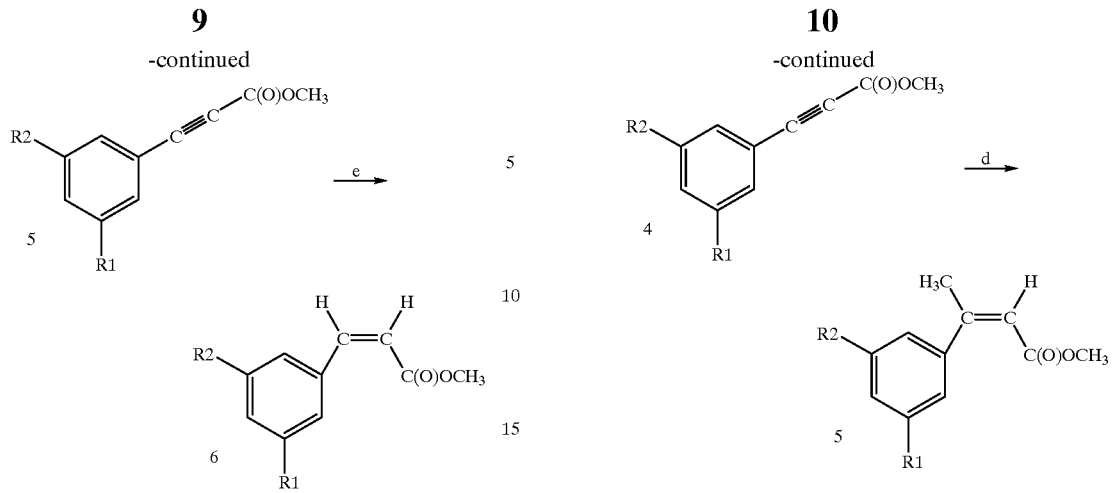

A halogenated phenyl derivative (preferably brominated or iodinated) where $R^1$ and $R^2$ are as in Formula 1 (1) is reacted with an acetylene such as trimethylsilylacetylene (a) using standard conditions for a coupling reaction (for example copper iodide, $PPh_3$, $Pd(PPh_3)_2Cl_2$, in diisopropylamine) to replace the bromine with acetylene preferably at 0 degrees C. to room temperature (2). The silyl group is hydrolyzed with a strong base such as potassium hydroxide and a solvent mixture, preferably an ether, diethyl ether, or tetrahydrofuran and a suitable aqueous solvent such as a lower alcohol (preferably methanol) and water (b). The resulting acetylene (3) is reacted with a strong base such as lithium bis(trimethylsilyl)amide and $CO_2$ (c) to obtain the carboxylic acid (4). The acid is esterified with a standard esterifying agent (d), for example diazomethane can be used to obtain the methyl ester (5). The triple bond is then reduced to a cis double bond under standard conditions for such reductions, for example with $H_2$ over Lindlar's catalyst (e), to obtain the (Z) or cis compound (6).

Scheme 2

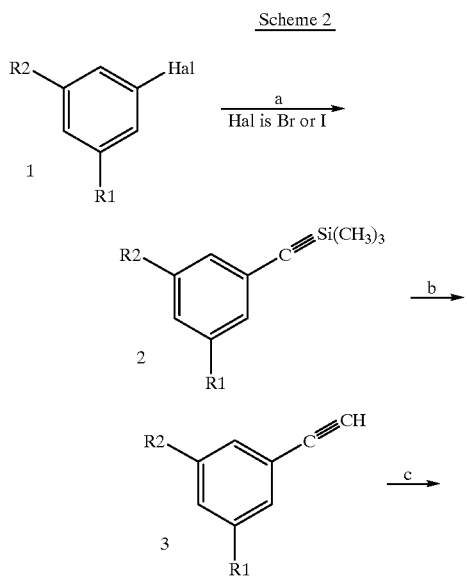

A halogenated phenyl derivative (preferably brominated or iodonated) where $R^1$ and $R^2$ are as in Formula 1 (1) is reacted with an acetylene such as trimethylsilylacetylene (a) using standard conditions for a coupling reaction (for example copper iodide, $PPh_3$, $Pd(PPh_3)_2Cl_2$, in diisopropylamine) to replace the bromine with acetylene (2). The silyl group is hydrolyzed with a strong base such as potassium hydroxide and a mixed solvent, preferably ether, diethyl ether, or tetrahydrofuran, and a suitable aqueous solvent such as a lower alcohol (preferably methanol) and water (b). The resulting acetylene (3) is reacted with a strong base such as n-butyl lithium and methylchloroformate in an aprotic solvent such as tetrahydrofuran (c) to obtain the ester (4). The tri-substituted cis double bond is obtained by reacting (4) with dimethyl copper lithium in an aprotic solvent such as tetrahydrofuran and ethyl acetate, preferably at about −70 degrees C. (d), to obtain the (Z) or cis compound (5).

Scheme 3

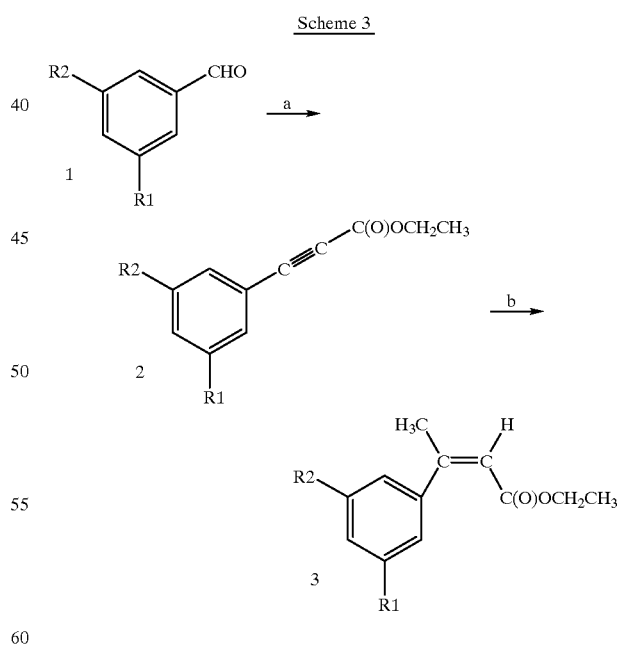

A benzaldehyde derivative where $R^1$ and $R^2$ are as in Formula 1 (1) is reacted with an acetate such as triethyl-2-iodo-phosphonoacetate using standard conditions for a Horner reaction using a base such as sodium hydride in dimethoxyethane preferably at −78 to 0 degrees C. The products of that reaction are reacted with lithium bis(trimethylsilyl)amide in tetrahydrofuran (a) to fully convert the intermediate vinyl iodide into the acetylene (2). The tri-substituted cis double bond is generated by reacting (2) with dimethyl copper lithium in tetrahydrofuran preferably at about −70 degrees C. (b) to obtain the (Z) or cis compound (3).

Scheme 4

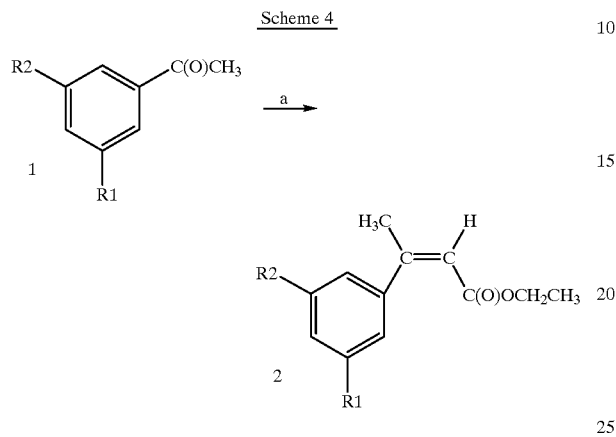

An acetophenone derivative where $R^1$ and $R^2$ are as in Formula 1 (1) is reacted with a Horner reagent (a) such as trialkyl 2-phosphonoalkanoate, (e.g. triethyl phosphonoacetate when R4 is H or triethyl-2-phosphonoproprionate when R4 is CH₃,)using standard conditions for a Horner reaction (for example potassium t-butoxide), to obtain the ester (2) as a mixture of E/Z isomers. The resulting E and Z (trans and cis) isomers are then separated by standard methods.

Scheme 5

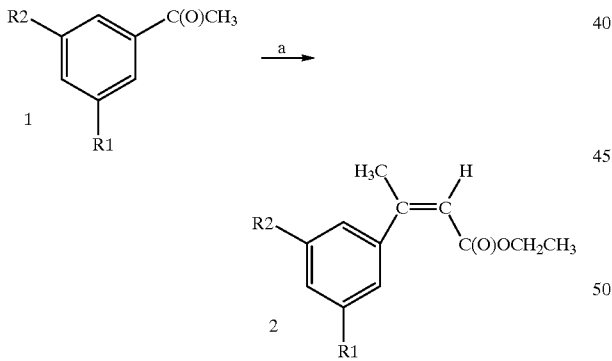

An acetophenone derivative where $R^1$ and $R^2$ are as in Formula 1 (1) is reacted with ethyl (trimethylsilyl)acetate (a) using standard conditions for a Peterson olefination reaction, using a strong base such as lithium diisopropylamide, or an alkyllithium in aprotic ether solvents, such as THF or ether, to obtain the ester (2), as a mixture of E/Z isomers. The resulting E and Z isomers are then separated by standard methods.

Schemes 4 and 5 are direct but the product is a mixture of isomers which then require separation, whereas the other Schemes produce the (Z) or cis isomer only.

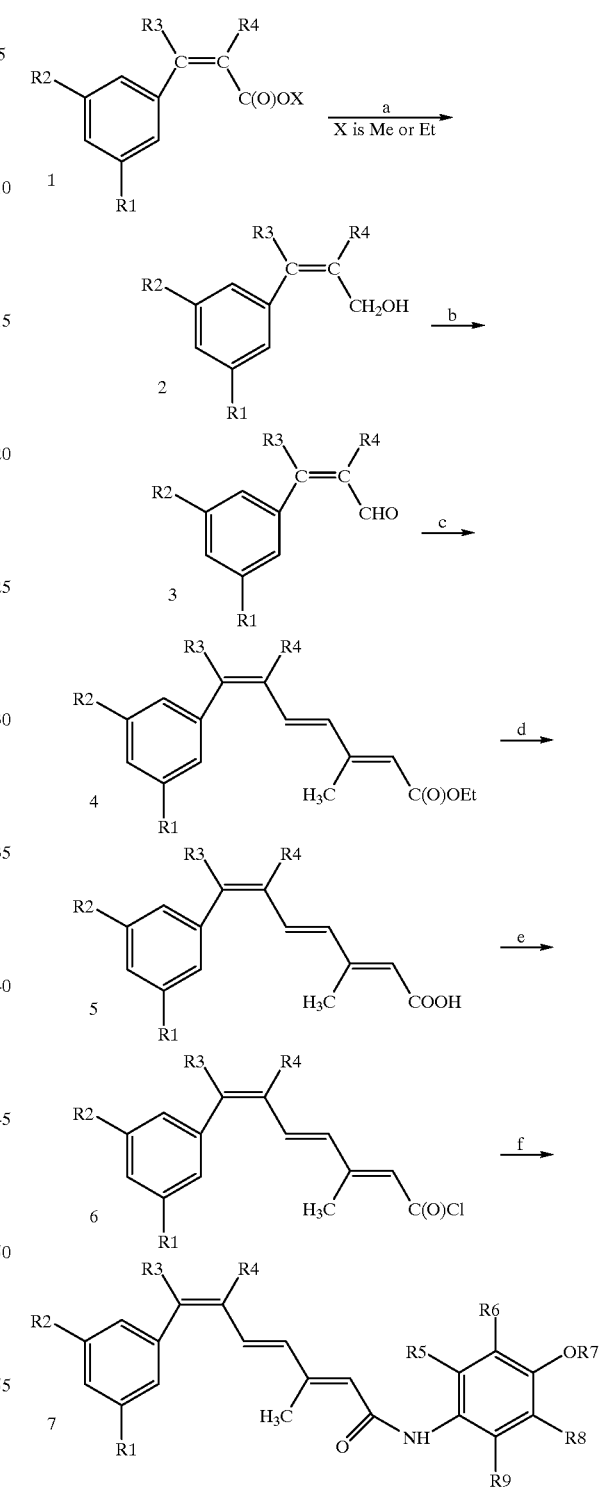

The methyl or ethyl (Z) propenoic acid ester of the previous schemes (1) is reduced to the corresponding alcohol (2) under standard conditions using an agent for reducing esters to alcohols, for example lithium aluminum hydride or diisobutylaluminum hydride (a) in a suitable solvent such as toluene, ether or other hexanes, preferably at about −30 to 0 degrees C. The alcohol (2) is oxidized using a suitable agent such as manganese dioxide (b) to the aldehyde (3). The aldehyde is reacted with 3-methyl-4-phosphonocrotonate and a suitable base such as lithium bis(trimethylsilyl)amide, preferably at about −70 to about 5 degrees C. (c) to obtain the ester (4). The ester is reacted with a hydrolyzing agent such as strong base, for example potassium or sodium hydroxide in an aqueous solvent such as water and lower alcohol (e.g. methanol or ethanol) preferably at about 80 degrees C. (d) to obtain the carboxylic acid (5). The carboxylic acid is reacted with an agent for generating acid chlorides such as dimethylchloroformamidinium chloride or with oxalyl chloride (e) to obtain the acid chloride (6). The acid chloride is reacted under standard conditions for conversion of an acid chloride to an amide (for example pyridine and dimethylformamide) with the following:

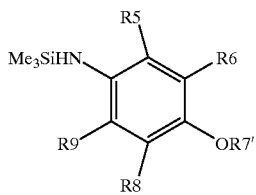

where R5, R6, R8 and R9 are as in Formula 1 and R7' is a standard hydroxy protecting group such as trimethyl silyl (f), and the 6(Z) or 6-cis amide (7) is obtained. Any of aminophenols with groups R5 through R9 can then be prepared using materials and methods well known to the skilled person.

The following Examples are provided to illustrate the invention and are not intended to limit it in any way.

EXAMPLE I

Syntheses

General: All reactions were carried out under an atmosphere of argon and protected from light. HPLC column was Waters Prep Pak Silica gel (Porasil) 15–20 um, 125 A.

IA) Preparation of N-(4-hydroxyphenyl)-(2E,4E, 6Z)-7-[3,5-bis(trifluoromethyl)phenyl]-3,7 dimethyl-2,4,6-heptatrienamide A solution of 1-[3,5-bis(trifluoromethyl)phenyl]-acetylene (31.0 g, 130 mmol) in 600 mL of THF was cooled to −40° C. and treated with lithium bis(trimethylsilyl)amide (1.0 M) (135 mL, 135 mmol). After stirring for a few minutes, gaseous carbon dioxide was bubbled into the cold solution via a cannula. When an excess has been added, the reaction was stirred at ambient temperature until it warmed to −20° C. The reaction was poured into 1.5 L of water and brought to pH 3 with aqueous phosphoric acid (50%). Brine was added and the product was extracted into chloroform (2×). The organic extracts were washed with water/brine, dried (MgSO$_4$), and had solvent removed to give 31 g of 3-[3,5-bis (trifluoromethyl) phenyl]-propynoic acid which solidified on standing and was not further purified. $^1$H NMR (CDCl$_3$) δ8.80(1H, broad), 8.06 (2H, s, aromatic), 7.98 (1H, s, aromatic).

The 3-[3,5-bis(trifluoromethyl)phenyl]-propynoic acid was dissolved in a mixture of THF and ether and treated with diazomethane until all acid was methylated. All solvent was removed and the resulting oil was purified by chromatography (10% ether/hexane) to give 30.5 g of 3-[3,5-bis (trifluoromethyl)phenyl]-propynoic acid methyl ester.

$^1$H NMR (CDCl$_3$) δ8.06 (2H, s, aromatic), 7.94 (1H, s, aromatic), 3.88 (3H, O—CH$_3$).

Copper (I) bromide-dimethyl sulfide complex (22.6 g, 110 mmol) was suspended in 1.2L of THF (dry) that had been degassed and placed under Ar. The stirred suspension was cooled to 0° C. and 1.4 M solution of MeLi in ether (157 mL, 220 mmol) was added dropwise. After stirring for 15 min., the reaction was cooled to −78° C. and the 3-[3,5-bis (trifluoromethyl)phenyl]-propynoic acid methyl ester in THF (150 mL) was added dropwise. The reaction mixture was stirred for 1 h at this temperature. The reaction is then poured directly into a well stirred THF (500 mL) solution containing 250 mL of 20% aqueous phosphoric acid. This was stirred at ambient temperature for 10 min and extracted with hexane. The organic extracts were combined, washed with water/brine, dried (MgSO$_4$), and solvent removed to give 35 g of 3-[3,5-bis(trifluoromethyl)phenyl]-3-methyl-2 (Z)-propenoic acid methyl ester which was not purified, but reduced directly.

$^1$H NMR (CDCl$_3$) δ7.83 (1H, s, aromatic), 7.72(2H, s, aromatic), 6.04 (1H, s, C2-H), 3.59 (3H, O—CH$_3$), 2.21 (3H, s).

The ester, 3-[3,5-bis(trifluoromethyl)phenyl]-3-methyl-2 (Z)-propenoic acid methyl ester, (15 g, 53 mmol) was dissolved in hexanes (600 mL) and cooled to −40° C. and diisobutylaluminum hydride (DIBAH, 1M in hexanes, 122 mL, 122 mmol) was added dropwise. Once the addition was complete the temperature of the reaction was allowed to warm to +5° C. and treated with 10% aqueous solution of Rochelle salt (100 mL) and stirred for a further 2 h. The salts were filtered off and the filtrate washed with water, dried (MgSO$_4$), and concentrated to give 12 g of 3-[3,5-bis (trifluoromethyl)phenyl]-3-methyl-2(Z)-propen-1-ol:

$^1$H NMR (CDCl$_3$) δ7.77 (1H, s, aromatic), 7.61 (2H, s, aromatic), 5.88 (1H, t, C2-H), 4.02 (2H, O—CH$_2$), 2.14 (3H,s, CH$_3$).

The alcohol, of 3-[3,5-bis(trifluoromethyl)phenyl]-3-methyl-2(Z)-propen-1-ol, (12 g, 40 mmol) in EtOAc (800 mL) was added to a vigorously stirred suspension of MnO$_2$ (100 g) in EtOAc (800 mL). After stirring for 4 h at 32° C., the reaction mixture was cooled and filtered through a cake of celite. The filtrate was concentrated and the product purified by HPLC (15–20% EtOAc/hexanes) to give 8 g of 3-[3,5-bis(trifluoromethyl)phenyl]-3-methyl-2(Z)-propenal:

$^1$H NMR (CDCl$_3$) δ9.40 (1H, d, CHO), 7.93 (1H, s, aromatic), 7.72 (2H, s, aromatic), 6.24 (1H, d, C2-H), 2.37 (3H, s, CH$_3$).

Triethyl 3-methyl-4-phosphonocrotonate (13 g, 49 mmol) was dissolved in THF (600 mL) and cooled to −75° C. and treated with lithium bis(trimethylsilyl)amide (1M in THF, 45 mL, 45 mmol). The reaction was maintained at −75° C. while 3-[3,5-bis(trifluoromethyl)phenyl]-3-methyl-2(Z)-propenal (10.5 g, 37 mmol) in THF (50 mL) was added slowly. Stirring at −75° C. was continued for 0.5 h and then the reaction was allowed to warm slowly to +5° C. and poured into a dilute aqueous phosphoric acid solution. The product was extracted into hexanes and and the organic phase was washed with water, dried (Na$_2$SO$_4$), and concentrated to give the crude product. Purification of the desired isomer was accomplished by silica gel chromatography (5% ether/hexanes), followed by crystallization from hexanes to afford pure 7-[3,5-bis(trifluoromethyl)phenyl]-3,7-dimethyl-2(E), 4(E), 6(Z)-heptatrienoic acid ethyl ester:

$^1$H NMR (CDCl$_3$) δ7.82 (1H, s, aromatic), 7.70 (2H, s, aromatic), 6.49 (1H, dd, C5-H), 6.40 (2H, m, C4,6-H), 5.79 (1H, s, C2-H), 4.18 (2H, q, CH$_2$-O), 2.22 (3H, s, C3-CH$_3$), 2.13 (3H, s, C7-CH$_3$), 1.30 (3H, t, CH$_2$CH$_3$).

Conversion to 7-[3,5-bis(trifluoromethyl)phenyl]-3,7-dimethyl-2(E),4(E),6(Z)-heptatrienoic acid was carried out by treating 7-[3,5-bis(trifluoromethyl)phenyl]-3,7-dimethyl-2(E), 4(E), 6(Z)-heptatrienoic acid ethyl ester (0.46 g, 1.0 mmol) with a solution of ethanol (20 mL) and 10% aqueous KOH (4 mL) at reflux for 1.5 h. The solution was cooled and poured into 10% aqueous phosphoric acid (100 mL). This mixture was extracted with $CDCl_3$ and the $CHCl_3$ extract washed once with water, dried ($MgSO_4$), and concentrated to give a solid. The solid was crystallized from THF/hexanes to give 0.3 g of 7-[3,5-bis(trifluoromethyl)phenyl]-3,7-dimethyl-2(E),4(E),6(Z)-heptatrienoic acid:

$^1$H NMR ($CDCl_3$-DMSO) δ7.82 (1H,s, aromatic), 7.72 (2H, s, aromatic), 6.50 (1H, dd, C5-H), 6.40 (2H, m, C4,6-H), 5.80 (1H, s, C2-H), 2.24 (3H, s, C3 $CH_3$), 2.12 (3H, s, C7$CH_3$).

A solution of dry ether (60 mL) and DMF (1.4 g, 18 mmol) was cooled to 15° C. treated with oxalyl chloride (1.1 g, 8.7 mmol) and stirred for 15 min. All solvent was evaporated and the resulting dimethylchloroformamidinium chloride obtained as a white solid was suspended in DMF (50 mL) (dimethylchloroformamidinium chloride prepared according to the procedure in Helv. Chim. Acta 42, 1653 (1959)). To this was added 7-[3,5-bis(trifluoromethyl) phenyl]-3,7-dimethyl-2(E),4(E),6(Z)-heptatrienoic acid (0.95 g, 2.6 mmol) and the mixture was stirred for 3–4 h. This was cooled to 0° C. and treated over 10 min with a solution of O,N-bis-(trimethylsilyl)-4-aminophenol (4.8 g, 19 mmol) in DMF (50 mL). This was stirred for 1 h and poured into 5% aqueous KF (100 mL) and again stirred for 1 h. The aqueous mixture was extracted with ether, washed with water, dried ($MgSO_4$), and solvent removed to give an oil. This was purified by chromatography (HPLC-35% EtOAc/hexane) to give N-(4-hydroxyphenyl)-(2E,4E,6Z)-7-[3,5-bis(trifluoromethyl)phenyl]-3,7-dimethyl-2,4,6-heptatrienamide as a yellow solid. FABMS m/z (rel intensity) 455(M+H$^+$, base), 347 (50), 239 (22);

$^1$H NMR (DMSO) δ9.80(1H, s, NH), 9.18(1H, s, OH), 8.08 (1H, s, aromatic), 7.98(2H, s, aromatic), 7.41(2H, d, aromatic), 6.67(2H, d, aromatic), 6.6–6.4 (3H, broad, C4,5, 6-H), 6.02 (1H, s, C2-H), 2.26 (3H, s, C3 $CH_3$), 2.09 (3H, s, C7 $CH_3$).

IB) Preparation of N-(4-hydroxyphenyl)-(2E,4E, 6Z)-7-(3,5-dimethylphenyl)-3,7-dimethyl-2,4,6-heptatrienamide A solution of 5-bromo-m-xylene (19.4 g, 105 mmol) and diisopropylamine (100 mL) was degassed with argon and kept under an argon atmosphere. CuI (2.07 g, 10.7 mmol), $PPh_3$ (4.06 g, 15.3 mmol) and Pd($PPh_3$)$_2$$Cl_2$ (2.09 g, 2.92 mmol) were added followed by addition of trimethylsilylacetylene (12.3 g, 18 mL, 125 mmol). The reaction was heated to 75° C. for 2 h giving a dark brown viscous mixture. Additional trimethylsilylacetylene (6.15 g, 9 mL, 63 mmol), $PPh_3$ (2.04 g, 7.78 mmol), CuI (1.05 g, 5.51 mmol) and Pd($PPh_3$)$_2$$Cl_2$ (1.62 g, 2.31 mmol) were added and then the reaction was heated to 80° C. for 4 h. After cooling the reaction to room temperature, hexanes (300 mL) was added and the solution was filtered through celite. The hexane layer was washed with 1N HCl (600 mL), brine (300 mL), dried ($Na_2SO_4$), and concentrated to give crude 1-trimethylsilyl-2-(3,5-dimethylphenyl)-acetylene which was used for the next step.

$^1$H NMR($CDCl_3$) δ7.10 (2H, d), 6.94 (1H, s), 2.27 (6H, s), 0.23 (9H, s).

A solution of crude 1-trimethylsilyl-2-(3,5-dimethylphenyl)acetylene (105 mmol, theoretical maximum) in THF (70 mL) and MeOH (280 mL) was cooled in an ice/water bath during addition of 8N KOH (16 mL, 128 mmol) and water (25 mL) and the reaction was then removed from ice/water bath. After 1 h, approximately half of the organic solvent was removed in vacuo. Hexanes (1 L) and water (400 mL) were added. The organic layer was washed with saturated brine, dried ($Na_2SO_4$), and concentrated to give 11.3 g of 1-(3,5-dimethylphenyl)acetylene as a brown oil:

$^1$H NMR($CDCl_3$) δ7.12 (2H,s), 6.98 (1H,s), 3.00 (1H,s), 2.29 (6H, s). 1-(3,5-dimethylphenyl)acetylene (11.3 g, 86.3 mmol) in dry THF (80 mL) was cooled in dry ice/acetone bath under an argon atmosphere. The n-BuLi (1.6M in hexanes, 65 mL, 104 mmol) was added slowly, followed by methyl chloroformate (11.4 g, 9.4 mL, 121 mmol) addition. The reaction vessel was transferred to an ice/water bath and stirred for 1 h. Saturated sodium bicarbonate solution and ethyl ether were added to the reaction mixture. The organic layer was washed with saturated brine, dried ($Na_2SO_4$), and concentrated to give crude 3-(3,5-dimethylphenyl) propynoic acid methyl ester which was used for next step.

$^1$H NMR($CDCl_3$) δ7.22(2H,s), 7.08(1H,s), 3.83(3H,s), 2.29(6H,s).

In a 2 L 3-neck RB flask with an overhead mechanical stirrer and kept under an argon atmosphere, CuBreSMe$_2$ (21.2 g, 103 mmol) in 200 mL THF was cooled in a NaCl/ice/water bath to –5° C. MeLi (1.4M in Et$_2$O, 180 mL, 252 mmol) was added keeping the temperature below 10° C. The reaction vessel was then cooled with dry ice/isopropanol bath to –70° C. 3-(3,5-dimethylphenyl) propynoic acid methyl ester (16.2 g, 86.1 mmol) in 70 mL THF was added slowly so that the reaction temperature does not exceed –65° C. The cooling bath was removed and the reaction temperature allowed to warm to –35° C. The reaction mixture was then quickly added to a mixture of acetic acid (40 mL) and hexanes (300 mL) which had been cooled in a dry ice/isopropanol bath. A white precipitate in a light blue solution formed upon addition. The mixture was manually stirred with a paddle at room temperature. The precipitate was removed by filtration through a celite plug and the solids washed with Et$_2$O. After removal of most of the organic solvent in vacuo, the organic layer was washed with water (2×300 mL), saturated brine (300 mL), and dried ($Na_2SO_4$). Removal of solvent followed by filtration through a plug of silica gel with Et$_2$O as the mobile phase provided a yellow oil. (16.9 g, containing 8% undesired E isomer). Multiple purification steps using medium pressure liquid chromatography on silica gel with 4% Et$_2$O/hexanes mobile phase provided, 3-(3,5-dimethylphenyl)-3-methyl-2(Z)-propenoic acid methyl ester (1 1.8 g, 57.8 mmol, 55% yield for 4 steps)

$^1$H NMR($CDCl_3$) δ6.93(1H,s), 6.80(2H,s), 5.87(1H,d), 3.55(3H,s), 2.30(6H,s with fine splitting, 2 $CH_3$), 2.14(3H,s with fine splitting, $CH_3$).

Using a 2 L 3-neck RB flask with an overhead mechanical stirrer, 3-(3,5-dimethylphenyl)-3-methyl-2(Z)-propenoic acid methyl ester (14.9 g, 73 mmol) in Et$_2$O (418 mL) was cooled to –50° C. and kept under an argon atmosphere. Diisobutylaluminum hydride (DIBAH, 1.5M in toluene, 108 mL, 162 mmol) was added slowly. The reaction vessel was placed in an ice/water bath and kept at 0° C. and a 20% solution of Rochelle salt (585 mL) was added with continued vigorous stirring and the reaction was allowed to warm to room temperature. The organic layer was decanted off and followed by addition of an 8:2 hexanes/ Et$_2$O solution (1.25 L) to the aqueous layer. Following manual swirling of layers, the organic layer is decanted off. The combined organic layers were washed with saturated brine, dried (Na$_2$SO$_4$), and concentrated to provide 3-(3,5-dimethylphenyl)-3-methyl-2(Z)-propen-1-ol as an oil (15 g, 116% of theoretical yield) which was oxidized without further purification.

$^1$H NMR(CDCl$_3$) δ6.92 (1H, s); 6.78 (2H, s); 5.67 (1H, dt); 4.07 (2H, d); 2.31 (6H, s); 2.06 (3H, s with fine splitting).

In a 5L 3-neck RB flask with an overhead mechanical stirrer and kept under an argon atmosphere, MnO$_2$ (271 g, 3.12 mol) in Et$_2$O (3 L) was cooled to 10° C. 3-(3,5-dimethylphenyl)-3-methyl-2(Z)-propen-1-ol (17.8 g crude, 90.8 mmol maximum) in Et$_2$O (250 mL) was added slowly to a MnO$_2$ suspension. The reaction temperature was allowed to warm to room temperature over 1 h. Additional MnO$_2$ (30.7 g, 353 mmol) was added. After 20 minutes the reaction was complete by TLC. The mixture was filtered through celite, the filtrate dried (Na$_2$SO$_4$), and concentrated to provide 3-(3,5-dimethylphenyl)-3-methyl-2(Z)-propenal as an oil (14.1 g, unpurified product 89% maximum yield for 2 steps).

$^1$H NMR(CDCl$_3$) δ9.48(1H,d); 7.04(1H,s); 6.91(2H,s); 6.10(1H,d); 2.35(6H,s); 2.29(3H,s).

In a 5 L 3-neck RB flask with an overhead mechanical stirrer and kept under an argon atmosphere, triethyl 3-methyl-4-phosphonocrotonate (43.6 g, 165 mmol, 1:1 mixture of cis/trans) in THF (1.25 L) was cooled to −70° C. with a dry ice/acetone bath. Lithium bis(trimethylsilyl) amide (1M in THF, 116 mL, 116 mmol) was added slowly. The reaction was stirred for 10 minutes and then 3-(3,5-dimethylphenyl)-3-methyl-2(Z)-propenal (16.4 g crude, 94.1 mmol) in THF (250 mL) was added slowly. The reaction was allowed to warm to −40° C. An ammonium chloride (55 g in 550 mL water) solution was added to reaction mixture, followed by addition of 3N phosphoric acid (163 mL) and stirring for 1 h at room temperature, Et$_2$O (1500 mL) was then added, followed by hexanes (4 L) and water (3 L). The organic layer was washed with saturated brine (500 mL), dried (Na$_2$SO$_4$), and concentrated to provide a brown oil (46.7 g) which was passed through a plug of silica gel with Et$_2$O/CH$_2$Cl$_2$/hexanes (3:20:77) as eluent to provide a mixture of isomers of E/Z isomers (8:2) at the 2,3- position, (24.7 g, 86.8 mmol, 92% yield for mixture). Medium pressure silica gel chromatography was used to obtain 90% pure 7-(3,5-dimethylphenyl)-3.7-dimethyl-2 (9:1E/Z),4(E),6(Z)-heptatrienoic acid ethyl ester (20.7 g, 90% yield) which was used for subsequent hydrolysis reaction.

$^1$H NMR(CDCl$_3$) δ6.96(s,1H), 6.87(s,2H), 6.73(dd,1H), 6.26(d,1H), 6.22(d,1H), 5.74(s,1H), 4.15(q,2H), 2.34(s,6H), 2.17(s,6H), 1.28(t,3H).

In a 1 L RB flask NaOH (10M, 50.7 mL) was added to a solution of 7-(3,5-dimethylphenyl)-3.7-dimethyl-2(9:1 E/Z),4(E),6(Z)-heptatrienoic acid ethyl ester (14.4 g, 50.6 mmol) in MeOH (70 mL) and THF (30 mL). The reaction was heated to 80° C. for 1 h and then placed in an ice/water bath. Cold 3N phosphoric acid solution (525 mL) was added to acidify the solution. Water (300 mL) was added, and the solution was extracted with Et$_2$O (1100 mL). The organic layer was washed with saturated brine, dried (Na$_2$SO$_4$), and concentrated to provide a yellow powder (12.4 g, 95%). Recrystallizations with hot THF/hexanes provided off white crystals of 7-(3,5-dimethylphenyl)-3.7-dimethyl-2(E),4(E), 6(Z)-heptatrienoic acid as a single isomer (8.64 g, 67% yield).

$^1$H NMR(CDCl$_3$) δ6.96 (s,1H), 6.87 (s, 2H), 6.76 (dd, 1H), 6.26 (d, 1H), 6.23 (d, 1H), 5.77 (s, 1H), 2.33 (s, 6H), 2.17 (s,6H); HRMS Calcd for C$_{17}$H$_{20}$O$_2$: 256.1463; found 256.1465.

Dimethylchloroformamidinium chloride (Helv. Chim. Acta 42, 1653 (1959)) (65.1 mmol) was dissolved in dry DMF (180 mL) and cooled in an ice/water bath. 7-(3,5-dimethylphenyl)-3,7-dimethyl-2(E),4(E),6(Z)-heptatrienoic acid (10.2 g, 39.7 mmol) in DMF (50 mL) was added, and the reaction was stirred at room temperature for 70 minutes. The solution of 7-(3,5-dimethylpheny)-3,7-dimethyl-2(E),4(E),6(Z)-heptatrienoyl chloride was cooled in an ice/water bath and used for the next step of the reaction sequence.

O,N-bis(trimethylsilyl)-4-aminophenol was prepared according to the procedure from patent WO 95/03274. O,N-bis(trimethylsilyl)-4-aminophenol (26.5 g, 105 mmol) in DMF (50 mL) and pyridine (19.3 mL, 238 mmol) was added to an ice/water bath cooled solution of 7-(3,5-dimethylphenyl)-3,7-dimethyl-2(E),4(E),6(Z)-heptatrienoyl chloride in DMF. The reaction was allowed to warm to room temperature and was complete after 30 min. Removal of the trimethyl silyl groups with KF (9.14 g, 157 mmol) in water (80 mL) was complete in 20 minutes. EtOAc (1400 mL) and water (1400mL) were added to reaction mixture. After separation, the organic layer was washed with saturated brine (500 mL), dried (Na$_2$SO$_4$), and concentrated to provide a brown oil (25.6 g). This material was chromatographed with 285 g of silica gel (230–400 mesh) using a 1:1 hexanes/EtOAc mobile phase which provided 13.6 g of product. Recrystallization from hot EtOAc/hexanes give pure N-(4-hydroxyphenyl)-(2E,4E,6Z)-7-(3,5-dimethylphenyl)-3,7-dimethyl-2,4,6-heptatrienamide (10.3 g, 75% yield).

$^1$H NMR(CDCl$_3$) δ7.37 (d,2H), 7.03 (s,1H), 6.95 (s,1H), 6.87 (s,2H); 6.77 (d,2H), 6.72 (dd,1H), 6.24 (d,1H), 6.23 (d,1H),5.75 (s,1H), 4.94 (broad,1H), 2.34 (s,6H), 2.23 (s,3H), 2.17 (s,3H); HRMS Calcd for C$_{23}$H$_{25}$NO$_2$: 347.1885; found: 347.1895.

IC) Preparation of N-(4-hydroxyphenyl)-(2E,4E, 6Z)-7-[3,5-bis(trifluoromethyl)phenyl]-3- methyl-2, 4,6-heptatrienamide The 3-[3,5-bis(trifluoromethyl)phenyl]propynoic acid methyl ester was prepared as given in experimental Example IA, steps 1 and 2).

The 3-[3,5-bis(trifluoromethyl)phenyl]propynoic acid methyl ester was dissolved in hexane (300 mL), treated with 1.0 g of Lindlar catalyst, and reduced under 1 atm of hydrogen at 22° C. When 1.1 eq. of hydrogen was absorbed the reaction was filtered through celite and the solvent was removed. The crude oil was purified by HPLC (5% ether/hexane) to give 3.5 g of 3-[3,5-bis(trifluoromethyl)phenyl]-2(Z)-propenoic acid methyl ester.

$^1$H NMR (CDCl$_3$) δ8.02 (2H, s, aromatic), 7.83 (1If, s, aromatic), 7.00 (1H, d, C3-H), 6.17 (1H, d, C2-H), 3.73 (3H, O—CH$_3$).

3.5 g (11 mmol) of 3-[3,5-bis(trifluoromethyl)phenyl]-2 (Z)-propenoic acid methyl ester was dissolved in 350 mL of hexane. This was cooled to −40° C. under Ar and diisobutylaluminum hydride (DIBAH 1.0 M in hexane, 35 mL, 35 mmol) was added slowly. After the addition was complete, the reaction was stirred and allowed to warm slowly to +5° C. The reaction was then treated with 50 mL of a 30% aqeuous Rochelle salt solution, 100 mL of ether and stirred at 30–35° for 2 h. The organic extracts were washed with water, dried (MgSO$_4$), and the solvent was removed to give 3.0 g 3-[3,5-bis(trifluoromethyl)phenyl]-2(Z)-propen-1-ol as an oil:

$^1$H NMR (CDCl$_3$) δ7.80 (1H, s, aromatic), 7.68 (2H, s, aromatic), 6.62 (1H, d, J=10 Hz), 6.12 (1H, dd, J=10 and 6 Hz), 4.40 (2H, t, HO—CH$_2$-).

The 3-[3,5-bis(trifluoromethyl)phenyl]-2(Z)-propen-1-ol (3.0 g, 10 mmol) was dissolved in 300 mL of ether (dry) and added to a cooled (10° C.) well stirred slurry of MnO$_2$ (40 g) in 300 mL ether. This was stirred at ambient temperature for 1 h. The suspension was filtered and the filtrate was washed with THF. The organics were combined and the solvent removed to give 3-[3,5-bis(trifluoromethyl)phenyl]-2(Z)-propenal as an oil. This was not purified and was taken on to the next step:

$^1$H NMR (CDCl$_3$) δ9.88 (1H, d, J=4 Hz, CHO), 7.94 (1H, s, aromatic), 7.85 (2H, s, aromatic), 7.61(1H, d, J=8 Hz), 6.35 (1H, dd, J=8&4 Hz).

3.4 g (13 mmol) of triethyl 3-methyl-4-phosphonocrotonate was dissolved in 150 mL THF, cooled to −78° C., and treated with 12 mL (12 mmol) (1.0 M in THF) of lithium bis(trimethylsilyl) amide. While at −78° C., the aldehyde 3-[3,5-bis(trifluoromethyl) phenyl]-2(Z)-propenal (2.5 g, 9.3 mmol) in 5 mL THF was slowly added. This was stirred at −78° C. for 0.5 h. and stirred while allowing the temperature to warm to +15° C. This was poured into cold dilute aqueous phosphoric acid. The product was extracted into hexane and the organic portion washed with water, dried (Na$_2$SO$_4$), and the solvent removed to give a crude oil containing 4 isomers. Purification and isomer separation was accomplished by silica gel chromatography (5% ether/hexane) to give two isomers. The required E,E,Z isomer was crystalized from hexane to give 500 mg of 7-[3,5-bis(trifluoromethyl)phenyl]-3-methyl-2(E),4(E),6(Z)-heptatrienoic acid ethyl ester $^1$H NMR(CDCl$_3$) δ7.80(1H, s, aromatic), 7.78 (2H, s, aromatic), 6.96 (1H, dd, C6-H), 6.48–6.78 (3H, olefins), 5.78(1H, s, C2-H), 4.18 (2H, q, O—CH$_2$), 2.23 (3H, s, C3 CH$_3$), 1.30 (3H, t, CH$_3$).

7-[3,5-bis(trifluoromethyl)phenyl]-3-methyl-2(E),4(E),6(Z)-heptatrienoic acid ethyl ester (500 mg, 1.2 mmol) was dissolved in 50 mL of ethanol and treated with an aqueous solution of KOH (0.5 g KOH /5 mL water). This was refluxed for 1.5 h. The solution was cooled, poured into water and acidified with dilute phosphoric acid. The solid which precipitated was extracted into chloroform. The organic portion was washed with water, dried (Na,SO$_4$), and the solvent removed to give a solid which was crystallized from THF/hexanes to afford 7-[3,5-bis(trifluoromethyl) phenyl]-3-methyl-2(E),4(E),6(Z)-heptatrienoic acid.

$^1$H NMR (CDCl$_3$) δ7.79(1 H, s, aromatic), 7.77(2H, s, aromatic), 6.96 (1H, dd, J=11.5 Hz), 6.50–6.63 (3H, olefins), 5.89(1H, s, C2-H), 2.24 (3H, s, C3 CH$_3$).

A solution of dry ether (60 mL) and DMF (1.0 g, 12 mmol) was cooled to 15° C. treated with oxalyl chloride (0.7 g, 5.9 mmol) and stirred for 15 min. All solvent was evaporated and the resulting dimethylchloroformamidinium chloride (Helv. Chim. Acta 42, 1653 (1959)) as a white solid was suspended in DMF (10 mL).To this was added of 7-[3,5-bis(trifluoromethyl)phenyl]-3-methyl-2(E),4(E),6(Z)-heptatrienoic acid (0.90 g,2.6 mmol) and the mixture was stirred for 3 h. This was cooled to 0° C. and treated over 10 min with a solution of O,N-bis(trimethylsilyl)-4-aminophenol (1.6 g, 5.9 mmol) in 5 mL DMF. This was stirred for 1 h and poured into 15% aqueous KF (20 mL) and again stirred for 1 h. The aqueous mixture was extracted with ether, washed with water, dried (MgSO$_4$), and solvent removed to give an oil. This oil was purified by chromatography (40% ethyl acetate/hexane) to give N-(4-hydroxyphenyl)-(2E,4E,6Z)-7-[3,5-bis(trifluoromethyl) phenyl]-3-methyl-2,4,6-heptatrienamide as a yellow solid:

$^1$H NMR (DMSO/CDCl$_3$) δ8.50(1H, s, NH), 7.78(3H, s, aromatic), 7.31(2H, d, aromatic) 6.68(2H, d, aromatic) 6.48 (1H, —OH), 6.9–6.4 (3H, broad, C4,5,6-H), 5.92(1H, s, C2-H), 2.26 (3H, s, C3 CH$_3$).

ID) Preparation of N-(4-hydroxyphenyl)- (2E,4E, 6Z)-7-(3,5-dimethoxyphenyl)-3,7-dimethyl-2,4,6-heptatrienamide A 1L, 3-necked, round bottom flask equipped with a magnetic stirrer, argon inlet and addition funnel was charged with sodium hydride (60% in mineral oil, 2.53 g, 63.3 mmol) and anhydrous dimethoxyethane (60 mL). The grey slurry was cooled to 0° C. with an ice bath and triethyl phosphonoacetate (11.94 mL, 60.2 mmol) was added dropwise while maintaining the temperature below 10° C. To the resulting light brown clear solution at 0° C. was slowly added a solution of iodine (15.27 g, 60.2 mmol) in anhydrous dimethoxyethane (50 mL) while controlling the temperature under 10° C. The resulting brown mixture was stirred at about 10° C. for half an h. After re-cooling the reaction mixture to 0° C., sodium hydride (60% in mineral oil, 5.05 g, 126.3 mmol) was carefully added in two batches. The greenish yellow slurry was then stirred at 25° C. until hydrogen evolution ceased. After re-cooling the mixture to 0° C., a solution of 3,5-dimethoxybenzaldehyde (9.5 g, 57.2 mmol) in anhydrous dimethoxyethane (30 mL) was slowly added and the mixture was then warmed up to room temperature and stirred overnight. The light-brown mixture was concentrated in vacuo and was diluted with water (300 mL) and extracted with ethyl ether (2×400 mL). The combined organic layers were washed with saturated sodium thiosulfate solution, water, brine, dried (MgSO$_4$), and concentrated in vacuo to give a crude product as a light brown oil (18.65 g, exceeded theoretical yield). The crude product was taken up in hexanes and chromatographed over silica gel. Elution using hexanes (1.2 L)→30% ethyl acetate/hexanes gave a 2:1 mixture of 3-(3,5-dimethoxyphenyl)-2-propynoic acid ethyl ester and 3-(3,5-dimethoxylphenyl)-2-iodo-2-propenoic acid ethyl ester (12 g).

A 500 mL, 3-necked, round bottom flask equipped with a magnetic stirrer, thermometer and an argon inlet was charged with the 2:1 mixture of 3-(3,5-dimethoxyphenyl)-2-propynoic acid ethyl ester and 3-(3,5-dimethoxyphenyl)-2-iodo-2-propenoic acid ethyl ester obtained above and anhydrous tetrahydrofuran (100 mL). The mixture was cooled to −70° C. with a dry ice/acetone bath and lithium bis(trimethylsilyl)amide (1.0 M in THF, 15.8 mmol) was slowly added. The mixture was immediately warmed up to −20° C. and stirred for half an h when NMR analysis of an aliquot indicated incomplete conversion of 3-(3,5-dimethoxyphenyl)-2-iodo-2-propenoic acid ethyl ester into 3-(3,5-dimethylphenyl)-2-propynoic acid ethyl ester (only the E-isomer of 3-(3,5-dimethoxyphenyl)-2-iodo-2-propenoic acid ethyl ester remained unreacted). An additional amount of lithium bis(trimethylsilyl)amide (1.0 M in THF, 4.0 mL, 4.0 mmol) was added to the mixture at −20° C. and stirred for an additional one h. NMR analysis of an aliquot showed the presence of 3-(3,5-dimethoxyphenyl)-2-iodo-2-propenoic acid ethyl ester. The mixture was warmed up to 0° C. and stirred for 90 minutes. The reaction was quenched with saturated ammonium chloride solution (60 mL) and was stirred at room temperature for 10 minutes. The mixture was extracted with ethyl acetate (2×200 mL) and the combined organic layers were washed with water, brine, dried ($Na_2SO_4$), concentrated in vacuo to give the crude product as a oil (11.0 g). This material was chromatographed on a Prep-HPLC using 1:5 ethyl acetate/hexanes as the eluent. Concentration of the appropriate fractions gave 3-(3,5-dimethoxyphenyl)-2-propynoic acid ethyl ester (9.32 g, 93% yield) as a colorless oil:

$^1$H NMR(400 MHz, $CDCl_3$) δ6.73 (2H, broad s), 6.55 (1H, broad), 4.30 (2H,q), 3.79 (6H,s), 1.36 (3H, t). HRMS Calcd. for $C_{13}H_{14}O_4$: 234.09892. Found: 234.0900.

A 2 L, 3-necked, round bottom flask equipped with a magnetic stirrer, thermometer and argon inlet was charged with copper (I) bromide-dimethyl sulfide complex (10.63 g, 51.71 mmol) and anhydrous THF (450 mL). The slurry was cooled using a dry ice/acetone bath and MeLi (1.5M in diethyl ether, 69.0 mL, 103.5 mmol) was added at a rate such that the internal temperature was around −5° C. The clear colorless solution was then cooled to −70° C. with a dry ice/acetone bath. A solution of 3-(3,5-dimethoxyphenyl)-2-propynoic acid ethyl ester (9.32 g, 39.8 mmol) in anhydrous tetrahydrofuran (50 mL) was added slowly so that the reaction temperature did not exceed −65° C. After stirring at −70° C. for two h, the reaction mixture was quickly transferred to a chilled, constantly shaken mixture of acetic acid (75 mL) and hexanes (750 mL) in a separatory funnel. Water was added and the mixture was shaken vigorously to give a white slurry which upon standing separated into two layers. The bottom white slurry was filtered through celite and rinsed thoroughly with hexanes. The filtrate and the washings were combined and washed with water (3 times), brine and dried ($Na_2SO_4$). The top layer in the separatory funnel from above was washed with water (3 times), brine, dried ($Na_2SO_4$) and concentrated in vacuo to provide crude product (9.19 g, 92%) as a light brown oil used in the next step without further purification.

$^1$H NMR(200 MHz, $CDCl_3$) δ6.40 (t,2H), 6.33 (d,1H), 5.86 (d,1H), 4.01 (q,2H), 3.75 (s, 6H), 2.13 (s,3H), 1.09 (t,3H).

A 2 L, 3-necked, round bottom flask equipped with a magnetic stirrer, thermometer and argon inlet was charged with crude 3-(3,5-dimethoxyphenyl)-3-methyl-2(Z)-propenoic ethyl ester (10.42 g, 41.63 mmol) and hexanes (1000 mL). Diisobutylaluminum hydride (DIBAH, 1.0 M in hexane, 104 mL, 104 mmol) was added slowly to the reaction mixture while the temperature was maintained between −20° C. to −30° C. using a dry ice/acetone bath. The mixture was then warmed up to 0° C. and stirred for 75 minutes. A solution of Rochelle salt (30% solution, 60 mL) was added to the reaction mixture with vigorous stirring and the whole mixture was kept at 35° C. for 30 minutes. After stirring at room temperature for another 30 minutes, the clear hexane layer was decanted into a separatory funnel and was washed with water, brine, and dried ($Na_2SO_4$). The aqueous white emulsions left in the reaction flask were back-extracted with ethyl ether (4×150 mL). The combined organic extracts were washed with water, brine, dried ($Na_2SO_4$), and concentrated to provide crude 3-(3,5-dimethoxyphenyl)-3-methyl-2(Z)-propen-1-ol as a light brown viscous oil (8.68 g, >100%) which was used in the next step without further purification.

$^1$H NMR(400 MHz, $CDCl_3$) δ6.39 (1H, t), 6.33 (2H, d), 5.68 (1H, t), 4.09 (2H, d), 3.79(6H, s), 2.06 (3H, s). NRMS Calcd for $C_{2}H_{6}O_{3}$; 208.1099. Found: 208.1096.

A 2 L, 3-necked, round bottom flask equipped with an overhead mechanical stirrer, addition funnel and an argon inlet, was charged with activated $MnO_2$ (85%, 86.8 g, 849 mmol) in ethyl acetate (700 mL). A solution of crude 3-(3,5-dimethoxyphenyl)-3-methyl-2(Z)-propen-1-ol (8.68 g, 41.7 mmol) in ethyl acetate (160 mL) was added to the black suspension. The reaction mixture was stirred at room temperature for about three h. The mixture was filtered through celite and the filter cake was rinsed thoroughly with ethyl acetate (3 L). The combined filtrate was concentrated in vacuo to give a light brown oil (8.45 g, 98% crude yield). The crude oil was purified by Prep-HPLC using 15% ethyl acetate/hexanes as eluent. The appropriate fractions were combined and 3-(3,5-dimethoxyphenyl)-3-methyl-2(Z)-propenal was obtained as a light brown oil.

$^1$H NMR(200 MHz, $CDCl_3$) δ9.52 (1H, d), 6.47 (1H, t), 6.41 (2H, d), 6.07 (1H, d,), 3.79 (6H,s), 2.27 (3H,s).

A 2L, 3-necked, round bottom flask equipped with a magnetic stirrer, thermometer and argon inlet was charged with triethyl 3-methyl-4-phosphonocrotonate (freshly distilled, 14.75 g, 55.82 mmol) and anhydrous tetrahydrofuran (670 mL). To the above solution was slowly added lithium bis(trimethylsilyl)amide (1M in THF, 55.7 mL, 55.7 mmol) while the internal temperature was maintained at −40° C. with a dry ice/acetone bath.

After the addition was complete, the mixture was stirred at −40° C. for 15 minutes and was then further cooled to −70° C. A solution of crude 3-(3,5-dimethoxyphenyl)-3-methyl-2(Z)-propenal (6.38 g, 30.93 mmol) in anhydrous tetrahydrofuran (50 mL) was added slowly and the mixture was allowed to warm to 5° C. over a period of about two h. The reaction was quenched with a chilled solution of phosphoric acid (85%, 5 mL) in water (300 mL) and then diluted with hexanes (300 mL). The aqueous layer was extracted once with 1:1 ethyl ether/hexanes. The combined organic layers were washed with water, brine and dried with anhydrous sodium sulfate. Filtration and concentration in vacuo gave crude 3-(3,5-dimethoxyphenyl)-3,7-dimethyl-2(E),4(E),6(Z)-heptatrienoic acid ethyl ester as a brown oil. The crude oil was purified by Prep-HPLC using 15% ethyl acetate/hexanes as the eluent. The appropriate fractions were combined and concentrated to give 3-(3,5-dimethoxyphenyl)-3,7-dimethyl-2(E),4(E),6(Z)-heptatrienoic acid ethyl ester (9.68 g, 99% yield, ~80:20 E/Z isomers at C-2) as a light brown oil. The oil was dissolved in 5 mL of ethyl acetate and 100 mL of hexanes, the solution was kept in the freezer and filtered cold to give 2.83 g of white needles as the first crop. The mother liquor was recrystallized in the same fashion using 2.5 mL of ethyl acetate and 50 mL of hexanes to give 1.04 g as the second crop. The total amount of pure 3-(3,5-dimethoxyphenyl)-3,7-dimethyl-2(E),4(E),6(Z)-heptatrienoic acid ethyl ester was 3.87 g.

$^1$H NMR(400 MHz, $CDCl_3$) δ6.76 (1H, dd), 6.42 (1H,t), 6.40 (2H,d), 6.24 (1H,d), 6.22 (1H,d), 5.75 (1H,s), 4.15 (2H,q), 3.80 (6H,s), 2.18 (3H,s), 2.16 (3H,s), 1.28 (3H,t). HRMS Calcd. for $C_{19}H_{24}O_4$: 316.1675. Found: 316.1673.

A 500 mL, one-necked, round bottom flask equipped with a magnetic stirrer, water condenser and argon inlet was charged with recrystallized 3-(3,5-dimethoxyphenyl)-3,7-dimethyl-2(E),4(E),6(Z)-heptatrienoic acid ethyl ester (3.87 g, 12.23 mmol) and ethanol (190 proof, 110 mL). A solution of potassium hydroxide (2.21 g, 39.39 mmol) in water (22 mL) was then added and the mixture was heated to 80° C. for 90 minutes. The reaction mixture was cooled in an ice bath and a chilled solution of 1M phosphoric acid was then added slowly until the pH of the solution was approximately 3. The white slurry was extracted with 1:1 ethyl acetate/ethyl ether twice. The combined organic extracts were washed with water, brine and dried over anhydrous sodium sulfate. Filtration and concentration in vacuo gave a light yellow solid. The solid was dissolved in THF and was plugged through a short column of silica gel using ethyl acetate as eluent. Concentration of the appropriate fractions gave 3-(3,5-dimethoxyphenyl)-3,7-dimethyl-2(E),4(E),6(Z)-heptatrienoic acid (3.45 g, 98% yield) as a yellow solid and was used in the next step without further purification. (56% yield in two steps, including saponification and purification from mother liquors, from 3-(3,5-dimethoxyphenyl)-3,7-dimethyl-2(Z)-propenal.

$^1$H NMR(200 MHz, CDCl$_3$) δ6.78 (1H,dd), 6.42 (1H,t), 6.39 (2H,d), 6.25 (1H,d), 6.21 (1H,d), 5.75 (1H,s), 3.79 (6H,s), 2.18 (3H,s), 2.16 (3H,s).

A 500 mL, one-necked, round bottom flask equipped for magnetic stirring and argon inlet was charged with oxalyl chloride (1.74 mL, 19.95 mmol) and ether (50 mL). The solution was cooled in a dry ice/acetone bath and anhydrous dimethylformamide (1.62 mL, 20.92 mmol) was slowly added (Helv. Chim. Acta 42, 1653 (1959)). After the addition was complete, the mixture was warmed up to 0° C. and stirred for thirty minutes. The volatiles were removed carefully in vacuo and the flask containing dimethylchloroformamidinium chloride was filled with argon. To the dimethylchloroformamidinium chloride was added anhydrous dimethylformamide (50 mL) and a solution of crude 3-(3,5-dimethoxyphenyl)-3,7-dimethyl-2(E),4(E),6(Z)-heptatrienoic acid (3.45 g, 11.96 mmol) in anhydrous dimethylformamide (35 mL). The reaction was stirred at room temperature for 90 minutes. The resulting clear solution was cooled down to 0° C. and a solution of O,N-bis(trimethylsilyl)-4-aminophenol (7.98 g, 31.48 mmol) in anhydrous dimethylformamide (18 mL) was added while maintaining the temperature below 12° C. Immediately after the addition of O,N-bis(trimethylsilyl)-4-aminophenol, pyridine (5.8 mL, 71.71 mmol) was added and the mixture was stirred at room temperature for 150 minutes. The mixture was re-cooled to 0° C. and a solution of potassium fluoride (2.74 g, 47.2 mmol) was added and the mixture was vigorously stirred for 1 h at room temperature. The reaction mixture was diluted with water (450 mL) and extracted with ethyl acetate (450 mL) and hexanes (200 mL). The organic layer was washed with 1N phosphoric acid (2×200 mL), water, brine, and dried (Na$_2$SO$_4$). The combined aqueous washes were back-extracted with ethyl acetate (2×250 mL). The combined organic layers were washed with water, brine, dried (Na$_2$SO$_4$), and concentrated to give a dark brown foam. The material was chromatographed on a Prep-HPLC using 45% ethyl acetate/hexanes as eluent. Concentration of the appropriate fractions gave N-(4-hydroxyphenyl)-(2E,4E,6Z)-7-(3,5-dimethoxyphenyl)-3,7-dimethyl-2,4,6-heptatrienamide (4.24 g, 93% yield) as a yellow foam. Recrystallization from hot ethyl acetate/hexanes gave in two crops 2.61 g (57%) of N-(4-hydroxyphenyl)-(2E,4E,6Z)-7-(3,5-dimethoxyphenyl)-3,7-dimethyl-2,4,6-heptatrienamide, mp 162–163° C.

$^1$H NMR(200 MHz, CDCl$_3$) δ7.34 (2H,d), 7.05 (1H,broad s), 6.65–6.85 (3H,m), 6.40 (3H,bs), 6.15–6.30 (2H,m), 5.74 (1H,s), 4.98 (1H,s), 3.79 (6H,s), 2.22 (3H,s); HRMS Calcd. for C$_{23}$H$_{25}$NO$_4$: 379.1784. Found: 379.1779.

IE) Preparation of N-(4-hydroxyphenyl)-(2E,4E,6Z)-7-[3,5-bis(trifluoromethyl)phenyl]-3,6,7-trimethyl-2,4,6-heptatrienamide A solution of triethyl 2-phosphonopropionate (20 g, 84 mmol) was dissolved in 300 mL of THF and cooled to 0° C. and treated with potassium t-butoxide (1.0 M in THF) (80 mL, 80 mmol). After 5 min., a solution of 3-[3,5-bis(trifluoromethyl)phenyl]acetophenone (12 g, 47 mmol) in 20 mL THF was added and stirred at ambient temperature for 3 h. This was poured into water and extracted into hexane. The organic extracts were washed with water and brine, dried (MgSO$_4$), and solvent removed to give 15 g of crude 3-[3,5-bis(trifluoromethyl)phenyl]-2,3 dimethyl-2(E/Z)-propenoic acid ethyl ester which was purified into the individual isomers by HPLC (silica gel, 5% ether/hexane). 3-[3,5-bis(trifluoromethyl)phenyl]-2,3 dimethyl-2(Z)-propenoic acid ethyl ester $^1$H NMR (CDCl$_3$) δ7.80(1H, aromatic), 7.61(2H, s, aromatic), 3.85 (2H, q, CH$_2$), 2.13 (3H, s, CH$_3$), 2.08(3H, s, CH$_3$).

5.0 g (14.7mmol) of 3-[3,5-bis(trifluoromethyl)phenyl]-2,3 dimethyl-2(Z)-propenoic acid ethyl ester was dissolved in 300 mL of hexane. This was cooled to −20° C. under Ar. Diisobutylaluminum hydride (DIBAH-1.0 M in hexane) (35 mL, 35 mmol) was added slowly. After the addition was complete, the reaction was stirred at ambient temperature until it had reached 5° C. The reaction was then treated with 50 mL of a 30% aqueous Rochelle salt solution, 100 mL of ether and well stirred at 30–35° C. for 2 h. The organic extracts were washed with water, dried (MgSO$_4$), and the solvent was removed to give 3.0 g of 3-[3,5-bis(trifluoromethyl)phenyl]-2,3-dimethyl-2(Z)-propen-1-ol as a oil:

$^1$H NMR (CDCl$_3$) δ7.75 (1H, s, aromatic), 7.61 (2H, s, aromatic), 3.90(2H, s, CH$_2$—), 2.04 (3H, S, CH$_3$), 1.96 (3H, s, CH$_3$).

The alcohol 3-[3,5-bis(trifluoromethyl)phenyl]-2,3-dimethyl-2(Z)-propen-1-ol (4.0 g, 12 mmol) was dissolved in 200 mL of ethyl acetate and added to a cooled (10° C.) well stirred slurry of MnO$_2$ (40 g) in 200 mL ether. This was stirred at ambient temperature for 1 h. The suspension was filtered and the solids washed with THF. The organics were combined and solvent removed to give an oil. This was purified by HPLC (silica gel, 10% ethyl acetate/hexane) to give 3.4 g 3-[3,5-bis(trifluoromethyl)phenyl]-2,3-dimethyl-2(Z)-propenal:

$^1$H NMR(CDCl$_3$) δ9.40(1 H, s, aldehyde), 7.90 (1H, s, aromatic), 7.70 (2H, s, aromatic), 2.32(3H, s, CH$_3$), 1.96 (3H, s, CH$_3$).

4.0 g (15 mmol) of triethyl 3-methyl-4-phosphonocrotonate was dissolved in 180 mL THF, cooled to −78° C. and treated with lithium bis(trimethylsilyl)amide (1.0 M in THF, 14.5 mL, 14.5 mmol). While at −78° C., 3-[3,5-bis(trifluoromethyl)phenyl]-2,3-dimethyl-2(Z)-propen-1-al (3.4 g, 11.3 mmol) in 5 mL THF was slowly added. This was stirred at −78° C. for 0.5 hr, and stirred at ambient temperature until the temperature was 15° C. This was poured into cold dilute aqueous phosphoric acid. The product was extracted into hexane and the organic portion washed with water, dried Na$_2$SO$_4$, and the solvent removed to give a crude oil containing 4 isomers. Purification and isomer separation was accomplished by silica gel chromatography (5% either/hexane) to give two isomers.

The required isomer was then crystallized from hexane to give 500 mg of 7-[3,5-bis(trifluoromethyl)phenyl]-3,6,7-trimethyl-2(E),4(E),6(Z)-heptatrienoic acid ethyl ester:

$^1$H NMR (CDCl$_3$) δ7.80(1H, s, aromatic), 7.61 (2H, s, aromatic), 6.43 (2H, dd, C4 and C6-H), 5.71(1H, s, C2-H), 4.18 (2H, q, O—CH$_2$CH$_3$), 2.20 (3H, s, C3 methyl), 2.02 (3H, s, CH$_3$), 2.00(3H, s, CH$_3$), 1.30 (3H, t, O—CH$_2$CH$_3$).

The ester 7-[3,5-bis(trifluoromethyl)phenyl]-3,6,7-trimethyl-2(E),4(E),6(Z)-heptatrienoic acid ethyl ester (2.9 g, 6.5 mmol) was dissolved in 50 mL of ethanol and treated with an aqueous solution of KOH (0.5 g KOH/5 mL water). This was refluxed for 1.5 h. The solution was cooled, poured into water and acidified with dilute phosphoric acid. The solid which precipitated was extracted into chloroform. The organic portion was washed with water, dried (Na$_2$SO$_4$), and the solvent removed. This gave a solid which was crystallized from TLIF/hexane to give 7-[3,5-bis(trifluoromethyl) phenyl]-3,6,7-trimethyl-2(E),4(E),6(Z)-heptatrienoic acid.

$^1$H NMR (DMSO) δ8.07 (1H, s, aromatic), 7.78 (2H, s, aromatic), 6.96 (2H, dd, C4 and C5-H), 5.88 (1H, s, C2-H), 2.22 (3H, s, C3CH$_3$), 2.02(3H, s, CH$_3$), 1.93 (3H, s, CH$_3$).

A solution of dry ether (20 mL) and DMF (0.50 g, 6 mmol) was cooled to 15° C. treated with dimethylchloroformamidinium chloride (Helv. Chim. Acta 42, 1653 (1959)) (0.3 g, 2.4 mmol) and stirred for 15 min. All solvent was evaporated and the resulting white solid was suspended in DMF (20 mL). To this was added 7-[3,5-bis(trifluoromethyl) phenyl]-3,6,7-trimethyl-2(E),4(E),6(Z)-heptatrienoic acid (0.60 g, 1.6 mmol) and the mixture was stirred for 3 h. This was cooled to 0° C. and treated over 10 min with a solution of O,N-bis(trimethylsilyl)-4-aminophenol (1.1 g, 4.3 mmol) (CAS #52726-86-0) in 5 mL DMF. This was stirred for 1 h and poured into 15% aqueous KF (20 mL) and again stirred for 1 h. The aqueous mixture was extracted with ether, washed with water, dried (MgSO$_4$), and solvent removed to give an oil. This oil was purified by chromathography (40% ethyl acetate/hexane) to give N-(4-hydroxyphenyl)-(2E,4E, 6Z)-7-[3,5-bis(trifluoromethyl)phenyl]-3,6,7-trimethyl-2,4, 6-heptatrienamide as a yellow solid:

$^1$H NMR (DMSO) δ9.75 (1H, s, NH), 9.20 (1H, -OH), 8.18 (1H, s, aromatic), 7.89 (2H, s, aromatic), 7.40 (2H, d, aromatic) 6.88 (2H, d, aromatic), 6.42 (2H, dd, C4,5-H), 6.04 (1H, s, C2-H), 2.22 (3H, s, CH$_3$), 2.04 (3H, s, CH$_3$), 1.98 (3H, s, CH$_3$).

IF) Preparation of N-(4-hydroxyphenyl)- (2E,4E, 6Z)-7-(3,5-dibromophenyl)-3,7-dimethyl-2,4,6-heptatrienamide A stirred solution of triethylphosphonoacetate (28 g, 125mmol) in dimethoxyethane (DME) was cooled to 5° C. and treated with NaH (55% in oil, 5.9 g, 135 mmol). When hydrogen evolution had ceased, a solution of iodine (32 g, 125 mmol) in 150 mL of DME was added dropwise. The reaction was then cooled to −20° C. and lithium bis (trimethylsilyl)amide (1.0 M THF, 125 mL, 125mmol) was added dropwise. This was stirred at −10° C. for 10 minutes and a solution of 3,5-dibromobenzaldehyde (33.0 g, 125mmol) in 150 mL of DME was added. This was stirred at ambient temperature for 1 h and 40–45° C. for 4 h. The reaction was poured into cold water and extracted into hexane. The organic portion was washed with water and brine. This was dried (MgSO$_4$) and had solvent removed to give a heavy oil. This was purified by HPLC (10% ethyl acetate/hexane) to give a mixture of iodoolefin isomers. This material was taken to the next step.

A stirred solution of 2-iodo-3-(3,5-dibromophenyl)-2(E, Z)-propenoic acid ethyl ester (44 g, 96 mmol) in THF (700 mL) was cooled to −75° C. and treated dropwise with lithium bis(trimethylsilyl)amide (1.0 M THF, 100 mL, 100 mmol). The temperature was carefully raised to −30° C. and poured into water and extracted into hexane. This was dried (MgSO$_4$) and solvent removed to give a thick oil. Purification by HPLC (3% ether/hexane) gave pure 3-(3,5-dibromphenyl)-2-propynoic acid ethyl ester.

$^1$H NMR (CDCl$_3$) δ7.73 (1H, d, aromatic), 7.65 (2H, d, aromatic), 4.30 (2H, q, OCH$_2$), 1.35(3H, t, CH$_3$).

Copper (I) bromide-dimethyl sulfide complex (20.7 g, 101 mmol) was suspended in 1.0 L of THF (dry) that had been degassed and placed under Ar. The stirred suspension was cooled to −5° C. and 1.5M solution of methyllithium in ether (137 mL, 205 mmol) was added. After stirring for 10 minutes, the reaction was cooled to −78° C. and 3-(3,5-dibromophenyl)-2-propynoic acid ethyl ester (31 g, 91 mmol) in THF (150 mL) was added dropwise. The reaction mixture was stirred at −65 to −60° C. for 2 h. The reaction was then poured directly into a well stirred hexane (500 mL) solution containing 100 mL of acetic acid. This was stirred at ambient for 10 minutes, then washed with water, brine, and dried (MgSO$_4$) and solvent removed. Purification by HPLC (5% EtOAc/Hexane) gave 14 g of 3-(3,5-dibromophenyl)-3-methyl-2-(Z)-propenoic acid ethyl ester.

$^1$H NMR (CDCl$_3$) δ7.61 (1H, s, aromatic), 7.25 (2H, s, aromatic), 5.92 (1H, s, C2-H), 4.01 (2H, q, CH$_2$), 2.13 (3H, s, CH$_3$), 1.11(3H, t, CH$_3$).

The 3-(3,5-dibromophenyl)-3-methyl-2-(Z)-propenoic acid ethyl ester (14 g, 41 mmol) was dissolved in hexane (1.1 L) and cooled to −40° C. This was treated dropwise with DIBAH (90 mL, 1.0 M in hexanes) and stirred at ambient until the temperature reached +5° C. This was treated with an aqueous solution of 10% Rochelle salt (100 mL) and stirred for 2 h. The salts were filtered and the organic residue washed with water, dried (MgSO$_4$), and the solvent removed to give 12 g of 3-(3,5-dibromophenyl)-3-methyl-2(Z)-propen-1 ol:

$^1$H NMR (CDCl$_3$) δ7.58 (1H, s, aromatic), 7.25(2H, s aromatic), 5.75 (1H, t, C2-H), 4.05 (2H, d, CH$_2$—O), 2.04 (3H, s, CH$_3$).

3-(3,5-dibromophenyl)-3-methyl-2(Z)-propen-1-ol (12, g, 40 mmol) in ethyl acetate (200 mL) was added to a well stirred suspension of MnO$_2$ in ethyl acetate (1.8L). After 2 h at 35° C., this was cooled, filtered through celite, and the solvent removed. This was purified by HPLC (10–15% Ethyl Acetate/Hexane) to give 9.4 g of 3-(3,5-dibromophenyl)-3-methyl-2(Z)-propenal.

$^1$H NMR (CDCl$_3$) δ9.45 (1H, d, aldehyde), 7.71 (1H, s, aromatic), 7.38 (2H, s, aromatic), 6.24 (1H, d, C2-H), 2.29 (3H, s, CH$_3$).

10.6 g (40 mmol) of triethyl 3-methyl-4-phosphonocrotonate was dissolved in 500 mL THF, cooled to −78° C. and treated with 36 mL (36 mmol/1.0 M in THF) of lithium bis(trimethylsilyl)amide. While at −78° C., 3-(3, 5-dibromophenyl)-3-methyl-2(Z)-propenal (9.3 g, 31 mmol) in 50 mL THF was slowly added. This was stirred at −78° C. for 0.5 h and stirred at ambient until the temperature was 10° C. This was poured into dilute aqueous phosphoric acid. The product was extracted into hexane and the organic portion washed with water, dried (Na$_2$SO$_4$), and had the solvent removed to give a crude oil. Purification and isomer separation was accomplished by silica gel chromatography (5% ether/hexane) to give 5.5 g of (2E,4E,6Z)-7-(3,5-dibromophenyl)-3,7-dimethyl-2,4,6-heptatrienoic acid ethyl ester.

$^1$H NMR (CDCl$_3$) δ7.60 (1H, s, aromatic), 7.31 (2H, s, aromatic), 6.52 (1H, dd, C5-H), 6.28 (2H, m, C4 and C6-H), 5.74 (1H, s, C2-H), 4.10 (2H, q, O—CH$_2$), 2.20 (3H, s, C3 CH$_3$), 2.13 (3H, s, C7 CH$_3$), 1.30 (3H, t, CH$_3$).

Conversion to (2E,4E,6Z)-7-(3,5-dibromophenyl)-3,7-dimethyl-2,4,6-heptatrienoic acid was carried out as given in Ia,b,c,d: A solution of (2E,4E,6Z)-7-(3,5-dibromophenyl)-3, 7-dimethyl-2,4,6-heptatrienoic acid ethyl ester (113 mg, 0.272 mmol) in 800 μL of THF, 800 μL of methanol, 70 μL of water, and 2.7 mL of ION NaOH solution was heated to 80° C. Workup involved neutralization of the cooled reaction solution with 3N $H_3PO_4$ (900 μL). Recrystallization from THF/hexanes gave 50 mg of (2E,4E,6Z)-7-(3,5-dibromophenyl)-3,7-dimethyl-2,4,6-heptatrienoic acid:

$^1$H NMR (CDCl$_3$) δ7.62 (1H, s, aromatic), 7.33 (2H, s, aromatic), 6.60 (1H, dd, C5-H), 6.32 (1H, d), 6.28 (1H, d), 5.80 (1H, s, C2-H), 2.20 (3H, s, C3 CH$_3$), 2.15 (3H, s, C7 CH$_3$); HRMS Calcd for $C_{15}H_{14}Br_2O_2$: 383.9361; found 383.9360.

A solution of dry ether (30 mL) and DMF (0.5 g, 7 mmol) was cooled to 15° C. and then treated with oxalyl chloride (0.2 g, 1.5 mmol) and stirred for 15 min. All solvent was then removed and dimethylchloroformamidinium chloride (Helv. Chim. Acta 42, 1653 (1959)) as a white solid was suspended in DMF (5 mL). To this was added (2E,4E,6Z)-7-(3,5-dibromophenyl)-3,7-dimethyl-2,4,6-heptatrienoic acid (0.30 g, 0.8 mmol) and the mixture was stirred at room temperature for 3–4 h. The reaction was cooled to 0° C. and treated over a 10 min period with a solution of O,N-bis(trimethylsilyl)-4-aminophenol (0.6 g, 2.4 mmol) in DMF (5 mL). Once the addition was complete stirring was continued for 1 h and then it was poured into 5% aqueous KF (10 mL) and stirred a further 1 h. The aqueous mixture was extracted with ether, purified by HPLC using 35% EtOAc/hexanes as eluent to give N-(4-hydroxyphenyl)-(2E,4E,6Z)-7-(3,5-dibromophenyl)-3,7-dimethyl-2,4,6-heptatrienamide.

$^1$H NMR (DMSO) δ9.80 (1H,s, NH), 9.18 (1H, s, OH), 7.82 (1H, s, aromatic), 7.51 (2H, s, aromatic), 7.41 (2H, d, aromatic), 6.67 (2H, d, aromatic), 6.6–6.4 (3H, br m, C4,5,6-H), 6.00 (1H, s,C2-H), 2.16(3H, s, C3 CH$_3$), 2.13 (3H, s, C7 CH$_3$).

IG) Preparation of N-(4-hydroxyphenyl)-(2E,4E,6Z)-7-phenyl-3,7-dimethyl-2,4,6-heptatrienamide Ethyl(trimethylsilyl)acetate (4.2 g, 40 mmol) in 40 mL THF was cooled in a NaCl/ice/water bath to 0° C. and then lithium diisopropyl amide (2.0 M in heptane/THF/ethylbenzene, 18.2 mL, 36.3 mmol) was added slowly. The reaction vessel was then cooled in a dry ice/isopropanol bath to −70° C. and acetophenone (2.0 g, 16.5 mmol) was added to the reaction mixture. The cooling bath was removed and the reaction temperature allowed to warm to 0° C. and phosphoric acid (3N, 100 mL) was added to the reaction mixture at this temperature. The reaction mixture was then diluted with water and extracted with ether and the organic solution washed with saturated brine, dried (MgSO$_4$), and concentrated to give a yellow oil. Medium pressure silica gel chromatography using 3% ether/hexanes allowed separation of both isomers. Pure 3-phenyl-3-methyl-2(Z)-propenoic acid ethyl ester (604 mg):

$^1$H NMR (CDCl$_3$) δ7.12–7.40 (5H, m, aromatic), 5.90 (1H, s), 3.97 (2H, q, O—CH$_2$), 2.14 (3H, s, vinyl-CH$_3$),1.06 (3H, t, —CH$_3$).

3-Phenyl-3-methyl-2(Z)-propen-1-ol was prepared in the same manner as 3-(3,5-dibromophenyl)-3-methyl-2(Z)-propen-1-ol under section IF) above. 3-Phenyl-3 -methyl-2(Z)-propenoic acid ethyl ester (543 mg, 2.96 mmol) DIBAH (1.5 M in toluene, 5.9 mL, 8.9 mmol), yield of 423 mg of 3-phenyl-3-methyl-2(Z)-propen-1-ol:

$^1$H NMR (CDCl$_3$) δ7.1–7.40 (5H, m, aromatic), 5.71 (1H, dt), 4.08 (2H, d), 2.09 (3H, d), 1.25 (1H, bs, OH).

3-Phenyl-3-methyl-2(Z)-propenal was prepared in the same manner as 3-(3,5-dibromophenyl)-3-methyl-2(Z)-propenal under section IF) above. 3-Phenyl-3-methyl-2(Z)-propen-1-ol (400 mg, 2.7 mmol); MnO$_2$ (2.8 g, 32.3 mmol), 10 mL ether, yield 340 mg of 3-phenyl-3-methyl-2(Z)-propenal:

$^1$H NMR (CDCl$_3$) δ9.48 (1H, d, CHO), 7.20–7.45 (5H, m, aromatic), 6.14 (1H, d), 4.08 (2H, d), 2.32 (3H, s with fine splitting).

7-Phenyl-3,7-dimethyl-2(E),4(E),6(Z)-heptatrienoic acid ethyl ester was prepared in the same manner as of 7-(3,5-dibromophenyl)-3,7-dimethyl-2(E),4(E),6(Z)-heptatrienoic acid ethyl ester in section IF) above. Triethyl 3-methyl-4-phospnonocrotonate (433 mg, 1.64 mmol), in 3 mL THF, lithium bis(trimethylsilyl)amide (1M in THF, 1.5 mL, 1.5 mmol), 3-phenyl-3-methyl-2(Z)-propenal (200 mg, 1.37 mmol) in 2 mL of THF. Yield 270 mg of 7-phenyl-3,7-dimethyl-2(E),4(E),6(Z)-heptatrienoic acid ethyl ester:

$^1$H NMR (CDCl$_3$) δ7.23–7.45 (5H, m, aromatic), 6.70 (1H, dd), 6.26 (2H, d), 5.74 (1H, s), 4.26 (2H, q), 2.19 (3H, s), 2.16 (3H, s), 1.28 (3H, t).

7-Phenyl-3,7-dimethyl-2(E),4(E),6(Z)-heptatrienoic acid prepared in the same manner as 7-(3,5-dibromophenyl)-3,7-dimethyl-2(E),4(E),6(Z)-heptatrienoic acid in section IF) above. 7-Phenyl-3,7-dimethyl-2(E),4(E),6(Z)-heptatrienoic acid ethyl ester (259 mg, 1.01 mmol) in 4 mL MeOH, 0.5 mL THF with 1 mL of 10N NaOH. Crystallization afforded 93 mg of 7-phenyl-3,7-dimethyl-2(E),4(E),6(Z)-heptatrienoic acid:

$^1$H NMR (CDCl$_3$) δ7.41 (2H, t, aromatic), 7.32 (1H, t, aromatic), 7.25 (2H, d, aromatic), 6.73 (1H, dd), 6.29 (1H, d), 6.27 (1H, d), 5.76 (1H, s), 2.20 (3H, s), 2.17 (3H, s); HRMS Calcd for $C_{15}H^{16}O_2$: 228.1150; found 228.1152.

N-(4-hydroxyphenyl)-(2E,4E,6Z)-7-phenyl-3,7-dimethyl-2,4,6-heptatrienamide prepared in the same manner as N-(4-hydroxyphenyl)-(2E,4E,6Z)-7-(3,5-dibromophenyl)-3,7-dimethyl-2,4,6-heptatrienamide in section IF) above. Dimethylchloroformamidinium chloride (Helv. Chim. Acta 42, 1653 (1959)) (42.1 mg, 0.33 mmol) in 1 mL of DMF reacted with 7-phenyl-3,7-dimethyl-2(E),4(E),6(Z)-heptatrienoic acid (50 mg, 0.22 mmol) in 1 mL of DMF to afford the acid chloride. The acid chloride was reacted with O,N-bis(trimethylsilyl)-4-aminophenol (167 mg, 0.66 mmol) in 1 mL DMF, pyridine (106 mL, 1.32 mmol) to afford, following crystallization, 12 mg of N-(4-hydroxyphenyl)-(2E,4E,6Z)-7-phenyl-3,7-dimethyl-2,4,6-heptatrienamide:

$^1$H NMR (CDCl$_3$) δ7.40 (2H, d, aromatic), 7.22–7.40 (5H, m, aromatic), 7.03 (1H, br m), 6.77 (2H, d), 6.68 (1H,dd), 6.24 (1H, d), 5.75 (1H, s), 4.77 (1H, brs), 2.22 (3H, s),2.19 s); HRMS Calcd for $C_{21},H_{21}NO_2$: 319.1572; found 319.1576.

Example II

Pharmacological Activity

IIA. In vitro assays:

Compounds of formula I were tested for cell growth inhibition and apoptosis activity in cellular assays using the following cell lines:

ER+ breast carcinoma, human (ZR-75-1) obtained from ATCC (CRL 1500), were grown in Gibco's RPMI 1640 media supplemented with sodium pyruvate, 10% FBS and 13 ng/mL gentamicin. Cells were incubated at 37° C., 4.5% $CO_2$ and 95.5% humidified air.

ER− breast carcinoma, human (MDA-435) obtained from Dr. Janet Price, MDA Cancer Center, Houston, Tex., were grown in Gibco's RPMI 1640 media supplemented with sodium pyruvate, 10% FBS and 13 ng/mL gentamicin. Cells were incubated at 37° C., 4.5% $CO_2$ and 95.5% humidified air.

ER– breast carcinoma, human (MDA-231) obtained from ATCC (HTB 22), were grown in Eagle's MEM medium supplemented with non-essential amino acids, sodium pyruvate, and Earle's BSS, 10% FBS, and 13 ng/mL gentamicin. Cells were incubated at 37° C., 4.5% $CO_2$ and 95.5% humidified air.

Lung, large cell carcinoma, human (H1299), obtained from ATCC (CRL-5803), were grown in Gibco's Delbecco Minimum Essential media (DMEM), high glucose, supplemented with sodium pyruvate, 10% FBS and 13 ng/mL gentamicin. Cells were incubated at 37° C., 4.5% $CO_2$ and 95.5% humidified air.

Colorectal carcinoma, human (RKO) obtained from Dr. Bernie Vogelstein, were grown in Gibco's Delbecco Minimum Essential media (DMEM), high glucose, supplemented with sodium pyruvate, 10% FBS and 13 ng/mL gentamicin. Cells were incubated at 37° C., 4.5% $CO_2$ and 95.5% humidified air.

1. Cell growth inhibition: MTT Assay

The compounds of formula 1 were tested for ability to inhibit cell growth using the standard MTT assay, a tetrazolium-based assay which measures the viability of cells in culture. Cells were harvested upon reaching 70–80% confluency and pelleted. The cells were then resuspended in medium in which FBS was replaced with Hyclone's Charcoal/Dextran stripped FBS, and seeded (2 mL/well) into 6-well plates (Corning) at a density allowing for linear growth over a four day assay period. Compounds of formula 1 (10 mM stock in dimethylsulfoxide (DMSO)) were added 18–24 hours post-seeding. Compound dilutions were prepared in the appropriate growth media and added to the cells for final concentrations of 10, 3.3 and 1 $\mu$M in 0.1% DMSO. At 24, 48 and 72 hr. time points, MTT (3-[4,5-dimethylthiazol-2-yl-2,5-diphenyltetrazolium bromide) stock solution (5mg/mL in 1 PBS) was added to the cells plates (625 $\mu$L/well) which were then incubated for 2.5 hours. Liquid was aspirated from the wells and 1 mL/well of 95% ethanol was added to solubilize the formazan reaction product. The plates were shaken (Bellco Mini-Orbital Shaker) for 15 minutes. The solubilized formazan was then transferred (50 $\mu$ls) into a 96-well plate and the optical densities (OD) were measured (Bio-Tek Microplate Reader) at 570 nm and reference wavelength of 660 nm. Percentage of inhibition of cell growth was calculated according to the following formula:

$$\% \; IN = \frac{OD \; (untreated) - OD \; (treated)}{OD \; (untreated)} \times 100$$

The results are provided in Tables 1–3.

TABLE 1

Inhibition of Cell Growth in ZR-75-1 cells

| | | % inhibition[1] drug concentration ($\mu$M) | | |
|---|---|---|---|---|
| compound | hours | 1.0 | 3.3 | 10.0 |
| N-(4-hydroxyphenyl)-(2E,4E,6Z)-7-[3,5-bis(trifluoromethyl)phenyl]-3,7-dimethyl-2,4,6-heptatrienamide | 24 | 1.0 | 14.0 | 21.0 |
|  | 48 | 0 | 18.0 | 30.0 |
|  | 72 | 13.0 | 56.0 | 64.0 |
| N-(4-hydroxyphenyl)-(2E,4E,6Z)-7-[3,5- | 48 | 3.0 | 0 | 60.0 |

TABLE 1-continued

Inhibition of Cell Growth in ZR-75-1 cells

| | | % inhibition[1] drug concentration ($\mu$M) | | |
|---|---|---|---|---|
| compound | hours | 1.0 | 3.3 | 10.0 |
| bis(trifluoromethyl)phenyl]-3,6,7-trimethyl-2,4,6-heptatrienamide | 72 | 16.0 | 10.0 | 80.0 |

[1]% inhibition — % inhibition of cell growth compared to no drug control

TABLE 2

Inhibition of Cell Growth in MDA 231 cells

| | | % inhibition[1] drug concentration ($\mu$M) | | |
|---|---|---|---|---|
| compound | hours | 1.0 | 3.3 | 10.0 |
| N-(4-hydroxyphenyl)-(2E,4E,6Z)-7-[3,5-bis(trifluoromethyl)phenyl]-3,7-dimethyl-2,4,6-heptatrienamide | 24 | 18 | 30 | 26 |
|  | 48 | 39 | 35 | 61 |
|  | 72 | 46 | 62 | 71 |
| N-(4-hydroxyphenyl)-(2E,4E,6Z)-7-[3,5-bis(trifluoromethyl)phenyl]-3,6,7-trimethyl-2,4,6-heptatrienamide | 24 | 0 | 0 | 40 |
|  | 48 | 0 | 0 | 57 |
|  | 72 | 38 | 48 | 76 |
| N-(4-hydroxyphenyl)-(2E,4E,6Z)-7-[3,5-bis(trifluoromethyl)phenyl]-3-methyl-2,4,6-heptatrienamide | 24 | 22 | 33 | 37 |
|  | 48 | 42 | 51 | 50 |
|  | 72 | 50 | 68 | 73 |
| N-(4-hydroxyphenyl)-(2E,4E,6Z)-7-[3,5-bis(methyl)phenyl]-3,7-dimethyl-2,4,6-heptatrienamide | 24 | 50 | 51 | 58 |
|  | 48 | 60 | 70 | 72 |
|  | 72 | 81 | 82 | 85 |
| N-(4-hydroxyphenyl)-(2E,4E,6Z)-7-[3,5-bis(methoxy)phenyl]-3,7-dimethyl-2,4,6-heptatrienamide | 24 | 18 | 21 | 30 |
|  | 48 | 30 | 52 | 65 |
|  | 72 | 25 | 61 | 64 |
| N-(4-hydroxyphenyl)-(2E,4E,6Z)-7-[3,5-bis(bromo)phenyl]-3,7-dimethyl-2,4,6-heptatrienamide | 24 | 6 | 65 | 65 |
|  | 48 | 72 | 81 | 82 |
|  | 72 | 78 | 86 | 87 |
| N-(4-hydroxyphenyl)-(2E,4E,6Z)-7-[phenyl]-3,7-dimethyl-2,4,6-heptatrienamide | 24 | 45 | 57 | 58 |
|  | 48 | 67 | 80 | 81 |
|  | 72 | 76 | 87 | 88 |

[1]% inhibition — % inhibition of cell growth compared to no drug control

TABLE 3

Inhibition of Cell Growth in MDA 435 cells

| | | % inhibition drug concentration ($\mu$M) | | |
|---|---|---|---|---|
| compound | hours | 1.0 | 3.3 | 10.0 |
| N-(4-hydroxyphenyl)-(2E,4E,6Z)-7-[3,5-bis(trifluoromethyl)phenyl]-3, 7-dimethyl-2,4,6-heptatrienamide | 24 | 47 | 78 | 77 |
|  | 48 | 59 | 91 | 95 |
|  | 72 | 94 | 96 | 98 |
| N-(4-hydroxyphenyl)-(2E,4E,6Z)-7-[3,5 bis(trifluoromethyl)phenyl]-3,6,7-trimethyl-2,4,6-heptatrienamide | 24 | 3 | 67 | 68 |
|  | 48 | 3 | 95 | 96 |
|  | 72 | 4 | 98 | 99 |
| N-(4-hydroxyphenyl)-(2E,4E,6Z)-7-[3,5-bis(trifluoromethyl)phenyl]-3-methyl-2,4,6-heptatrienamide | 24 | 19 | 81 | 91 |
|  | 48 | 45 | 93 | 99 |
|  | 72 | 73 | 83 | 100 |
| N-(4-hydroxyphenyl)-(2E,4E,6Z)-7-[3,5-bis(methyl)phenyl]-3, -dimethyl-2,4,6-heptatrienamide | 24 | 56 | 53 | 53 |
|  | 48 | 95 | 92 | 98 |
|  | 72 | 95 | 94 | 91 |
| N-(4-hydroxyphenyl)-(2E,4E,6Z)-7-[3,5-bis(methoxy)phenyl]-3, -dimethyl-2,4,6-heptatrienamide | 24 | 21 | 36 | 25 |
|  | 48 | 64 | 61 | 61 |
|  | 72 | 86 | 87 | 87 |
| N-(4-hydroxyphenyl)-(2E,4E,6Z)-7-[3,5-bis(bromo)phenyl]-3, -dimethyl-2,4,6- | 24 | 27 | 28 | 37 |
|  | 48 | 70 | 66 | 70 |

TABLE 3-continued

Inhibition of Cell Growth in MDA 435 cells

| compound | hours | % inhibition drug concentration ($\mu$M) | | |
|---|---|---|---|---|
| | | 1.0 | 3.3 | 10.0 |
| heptatrienamide | 72 | 86 | 88 | 87 |
| N-(4-hydroxyphenyl)-(2E,4E,6Z)-7- | 24 | 3 | 3 | 2 |
| [phenyl]-3, -dimethyl-2,4,6- | 48 | 39 | 40 | 42 |
| heptatrienamide | 72 | 41 | 51 | 68 |

[1]% inhibition — % inhibition of cell growth compared to no drug control

These results indicate that compounds of formula 1 are capable of inhibiting cell growth. Percent (%) inhibition increases with concentration and with hours of incubation in ER− breast carcinoma cells and colorectal carcinoma cells. However, all the compounds tested cause reduction of cell growth. For example, Table 3 shows that N-(4-hydroxyphenyl)-(2E,4E,6Z)-7-[phenyl]-3,7-dimethyl-2,4,6-heptatrienamide inhibits the growth of MDA-435 cells 68% compared to the no drug control at 10 $\mu$M after 72 hours. This means that these cells treated with the compounds of formula 1 show a corresponding decrease in their conversion of substrate into formazan which is due to reduction in the amount of cell growth or induction of apoptosis.

2. Apoptosis: Cell death detection by ELISA:

Compounds of formula 1 were tested for the ability to cause apoptosis as follows:

a) Sample preparation

Cells and media were collected, cells were pelleted, resuspended in 100 $\mu$l lysis buffer (50 mM Tris-Cl (pH=8.0), 20 mM EDTA, 1% NP-40e) and incubated 30 minutes at 4° C. to lyse. Cell debris was spun down and an aliquot (30 $\mu$l) of the supernatant was removed for protein determination and stored at −20° C. An additional 280 $\mu$l of lysis buffer, was added, mixed thoroughly and spun down at 14,000 RPM for 10 minutes at 4° C. An aliquot was removed (180 $\mu$l) and the sample was stored at −20° C. until testing.

b) ELISA

A commercially available apoptosis detection kit, obtained from Boehringer Mannheim (Cat. No. 1544-674), was used as per the directions provided with the kit (Cell Death Detection ELISA). However, the protocol was modified in that a 1:40 to 1:100 dilution of sample was prepared, rather than the recommended 1:10 dilution, due to the increase in cell number used to prepare the sample extract and the subsequent increase in ELISA reactivity. The assay measures apoptosis by quantifying the amount of nucleosomal fragmentation from the extracts of cells treated with the test compounds (samples). These nucleosomal fragments, generated by the activation of endonucleases, are a known downstream effector of apoptosis. Antihistone antibodies are used to fix any nucleosomal fragments in the sample to the well of the microtiter plates. The sample is then incubated with anti-DNA antibodies conjugated to peroxidase and subsequently incubated with the peroxidase substrate, ABTS. The resulting colorimetric change is measured spectrophotometrically at 405/490nm.

c) Protein Determination

The total protein content of each sample was determined for the purpose of normalizing the ELISA values to amount of sample loaded. Microplate assay protocol described in the instruction manual, for (Biorad DC Assay, Cat.#500-0116) section 5.2. The protein concentrations were calculated based upon a linear regression curve.

d) ELISA assay calculations

Relative ELISA O.D. readings are determined by subtracting the ELISA plate background O.D. value. No drug control O.D. value (lysis buffer only) was subtracted from sample O.D. value. A correction coefficient (CC), based on the sample protein concentration compared to no drug control, was determined to correct the sample O.D. following subtraction of the background O.D. (BCS O.D.). The fold increase over no drug control is calculated and normalized to the total protein concentration of the samples by multiplying against the correction coefficient.

To determine the fold increase in ELISA O.D., obtain the following O.D. measurements:

ELISA plate background—lysis buffer only (EPB);

no drug treated control—cell sample treated with DMSO (NDT);

drug treated sample—cell sample treated with a compound of formula 1 (DT) Subtract EPB from NDT (NDT−EPB) and DT (DT−EPB). The fold increase of the treated over the control is then (DT−EPB)/(NDT−EPB).

To determine the total protein concentration of the samples, obtain the total protein concentration in mg/ul calculated using standard linear regression formula (y=mx+b) based on BSA standards. B=ELISA background. Protein concentration (PC)(mg/ml)=(sample absorbance−b)/x.

Correction coefficient (cc) is (NDT)(PC)/(DT)(PC).

Determine fold increase of ELISA (FI) normalized to total PC:

nDT is DT×cc (which is DT O.D. normalized to PC)

nNDT is NDT×cc (which is NDT O.D. normalized to PC)

FI normalized to PC is nDT/nNDT.

The results are shown in Table 4 below.

TABLE 4

| | | Induction of Apoptosis | | | | | | | | | | | |
|---|---|---|---|---|---|---|---|---|---|---|---|---|---|
| | | ZR-75-I Fold Induction[1] | | | MDA-435 Fold Induction[1] | | | RKO Fold Induction[1] | | | H1299 Fold Induction[1] | | |
| Compd | hrs | 10 uM (cont.[2]) | 3.3 uM | 1 uM | 10 uM (cont.[2]) | 3.3 uM | 1 uM | 10 uM (cont.[2]) | 3.3 uM | 1 uM | 10 uM (cont.[2]) | 3.3 uM | 1 uM |
| (2E,4E,6Z)-7-[3,5-bis(trifluoromethyl)phenyl] dimethyl- | 24 | 1 (1) | 1 | 1 | 1 (13) | 1 | 1 | ND | ND | ND | ND | ND | ND |
| | 48 | 1 (1) | 1 | 1 | 1 (15) | 1 | 1 | ND | ND | ND | ND | ND | ND |

TABLE 4-continued

| | | Induction of Apoptosis | | | | | | | | | | | |
|---|---|---|---|---|---|---|---|---|---|---|---|---|---|
| | | ZR-75-I Fold Induction[1] | | | MDA-435 Fold Induction[1] | | | RKO Fold Induction[1] | | | H1299 Fold Induction[1] | | |
| Compd | hrs | 10 uM (cont.[2]) | 3.3 uM | 1 uM | 10 uM (cont.[2]) | 3.3 uM | 1 uM | 10 uM (cont.[2]) | 3.3 uM | 1 uM | 10 uM (cont.[2]) | 3.3 uM | 1 uM |
| 2,4,6-heptatrienoic acid | 72 | 2 (9) | 1 | 1 | 2 (19) | 1 | 1 | ND | ND | ND | ND | ND | ND |
| N-(4-hydroxyphenyl)-(2E,4E,6[3,5-bis(trifluoromethyl)phenyl]dimethyl-2,4,6-heptatrienamide | 24 | 3 (2) | 2 | 2 | 6 (5) | 6 | 3 | 21 (8) | 14 | 2 | 2 (1) | 3 | 1 |
| | 48 | 15 (30) | 19 | 2 | 16 (10) | 10 | 3 | 23 (9) | 5 | 4 | 12 (15) | 10 | 1 |
| | 72 | 67 (47) | 69 | 2 | 34 (12) | 12 | 4 | 15 (5) | 1 | 1 | 20 (25) | 17 | 1 |

[1]fold induction - fold increase in apoptosis, compared to no drug control, after correcting to the amount of protein.
[2]cont. - a comparison of activity with the assays internal positive control 9-cis 4-HPR.

The results in Table 4 demonstrate that the compounds of formula 1 tested in this assay are able to induce apoptosis in ER+ and ER− breast carcinoma cells and colorectal carcinoma cells. For example N-(4-hydroxyphenyl)-(2E,4E,6Z)-7-[3,5-bis(trifluoromethyl)phenyl]-3,7-dimethyl-2,4,6-heptatrienamide results in significant induction of apoptosis at 24–48 h, whereas the corresponding acid, (2E,4E,6Z)-7-[3,5-bis(trifluoromethyl)phenyl]-3,7-dimethyl-2,4,6-heptatrienoic acid induces considerably lower amounts apoptosis only after 72 h. Thus example N-(4-hydroxyphenyl)-(2E,4E,6Z)-7-[3,5-bis(trifluoromethyl)phenyl]-3,7-dimethyl-2,4,6-heptatrienamide induces significant apoptosis in MDA-435 and RKO cell lines after 24 hours and additionally in ZR-75-1 cells after 48 hours.

IIB. In vivo assays

The compound N-(4-hydroxyphenyl)-(2E,4E,6Z)-7-[3,5-bis(trifluoromethyl) phenyl]-3,7-dimethyl-2,4,6-heptatrienamide was tested and found to decrease both tumor size and tumor number. Thus, compounds of formula 1 have efficacy against established nitrosomethylurea (NMU)-induced mammary tumors in rats. The induction of invasive mammary-tissue specific tumors in rats by NMU (Gullino et al., 1975) produces primarily estrogen-dependent carcinomas (Arafah et al., 1980) within as little as 4 weeks following a single, low-toxicity dose (McCormick et al., 1981) and results in a high percentage of tumor induction. The properties of the tumors induced in rats by NMU in this experimental model are representative of human mammary carcinoma and are invasive (McCormick et al., 1981).

Materials and Methods, 750 virgin female Sprague-Dawley rats 26 to 32 days of age (Harlan Laboratories) were housed in polycarbonate cages (3 rats/cage) and provided food and water ad libitum. Mammary tumors were induced essentially as previously described (Gullino et al., 1975 and McCormick et al., 1981). At the age of 50+/−3 days, each animal received a single dose (50 mg/kg body weight) of NMU (Sigma, St. Louis, Mo.) in 0.85% sodium chloride acidified to pH 5.0 with acetic acid. The carcinogen was administered with a 26 g needle i.v. via the tail vein in a 0.5 ml volume.

Rats were checked weekly starting 4 weeks after NMU administration for palpable tumors and those bearing at least one mammary tumor, palpable for 11 days or less, were entered into study on day 61 post-NMU administration. Fifteen animals were entered into treatment or control groups. Tumor diameters were measured weekly with calipers along their long and short axes and tumor volume was calculated from the ellipsoid formula, $(D \times d^2)/2$, where D is the long diameter and d is the short diameter. The days on which new palpable tumors arose or on which established tumors disappeared were noted along with anatomical position. Tumors which appeared in the same anatomical location at which a tumor had previously completely regressed were considered to be regrowths of the same tumor. Rats which developed ulcerations of tumors were immediately terminated from studies. All animals entered into groups were weighed daily on weekdays for 6 weeks.

N-(4-hydroxyphenyl)-(2E,4E,6Z)-7-[3,5-bis(trifluoromethyl)phenyl]-3,7-dimethyl-2,4,6-heptatrienamide was prepared in 4% ethanol, 8% PEG400, 7.2% Cremophor RH40 and 80% D5W and administered intraperitoneally in a 2.8 ml volume via a 21 g needle 5 times per week, q.d., for 4 weeks.

Results and Discussion.

For treatment of NMU-induced tumors in rats, solutions of the test compound N-(4-hydroxyphenyl)-(2E,4E,6Z)-7-[3,5-bis(trifluoromethyl)phenyl]-3,7-dimethyl-2,4,6-heptatrienamide were prepared daily in 4% ethanol, 8% PEG400, 7.2% Cremophor RH40 and 80% D5W.

These results (see Tables 5–7) demonstrate that the tested compound is capable of causing existing tumors to shrink, and, in addition, causes the number of tumors to decrease by eliminating first tumors and preventing additional tumors from arising, in animals treated with the compound.

TABLE 5

Effect of four week intraperitoneal administration of N-(4-hydroxyphenyl)-(2E,4E,6Z)-7-[3,5-bis)trifluoromethyl) phenyl-3,7-dimethyl-2,4,6-heptatrienamide (compound) on NMU induced first tumors in Sprague-Dawley rats

| Group | No. of first tumors regressing to unpalpable/ no. palpable at day 0 at weeks | | | | | |
|---|---|---|---|---|---|---|
| | 1 | 2 | 3 | 4 | 5 | 6 |
| vehicle control - 2.8 ml, 5x/wk | 0/22 | 0/22 | 1/21 | 0/20 | 0/19 | 0/15 |
| compound 25 mg/ kg/2.8 ml, 5x/wk | 7/20** | 5/19* | 3/19 | 4/19* | 4/18* | 5/18* |

Probability that the percentage of first tumors regressing to unpalpable is greater than the vehicle control group (Fisher Exact Test); *$p < 0.05$ and **$p < 0.005$

TABLE 6

Effects of four week intraperitoneal administration of N-(4-hydroxyphenyl)-(2E,4E,6Z)-7-[3,5-bis(trifluoromethyl)phenyl-3,7-dimethyl-2,4,6-heptatrienamide (compound) on the volume of NMU induced first tumors in Sprague-Dawley rats

| Group | Mean tumor volume ± SEM (mm³) at weeks | | | | | |
|---|---|---|---|---|---|---|
| | 1 | 2 | 3 | 4 | 5 | 6 |
| vehicle control - 2.8. ml, 5x/wk | 1600 ± 563 | 3684 ± 1330 | 6060 ± 2632 | 5176 ± 1490 | 8600 ± 2838 | 6485 ± 2375 |
| compound 25 mg/kg/2.8 ml, 5x/wk | 358 ± 243** | 801 ± 395* | 2162 ± 705 | 3370 ± 1022 | 5433 ± 1721 | 8052 ± 2584 |

Probability that the mean tumor volume per rat is significantly less than the vehicle control group (Wilcoxon Rank Sum Test); *$p < 0.05$ and **$p < 0.005$

TABLE 7

Effects of N-(4-hydroxyphenyl)-(2E,4B,6Z)-7 [3,5-bis(trifluoromethyl)phenyl-3,7-dimethyl-2,4,6-heptatrienamide (compound) administered intraperitoneally against NMU induced first mammary tumors in Sprague-Dawley rats*

| Tumor volume relative to day 0 | Weeks post treatment | | | | | |
|---|---|---|---|---|---|---|
| | 1 | | 2 | | 3 | |
| | vehicle | compound | vehicle | compound | vehicle | compound |
| regressed > 50% | 0 | 10 | 0 | 8 | 2 | 6 |
| static | 6 | 5 | 1 | 5 | 1 | 3 |
| progressed > 100% | 16 | 4 | 21 | 6 | 18 | 6 |
| total | 22 | 19 | 22 | 19 | 21^ | 19 |

*Compound administered in 4% ethanol 8% PEG400, 7.2% Cremophor RH40 and 80% D5W at 25 mg/kg/2.8 ml. q.d., 5x/wk for 4 wks; 3 of 15 rats treated succumbed to toxicity and were censored from the data.
^Decreases in number of total tumors over time is due to the sacrifice of animals whose tumors ulcerated.

What is claimed is:

1. A compound of formula

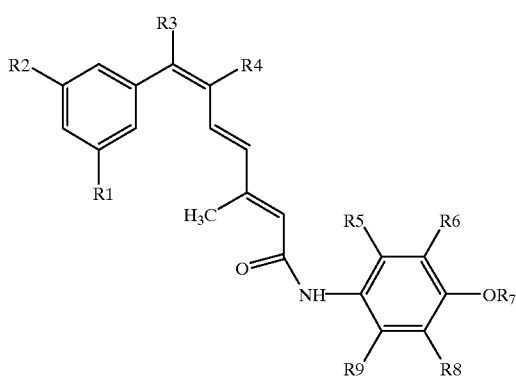

Formula 1 wherein $R^1$ and $R^2$ are independently hydrogen, halogen, alkyl, alkoxy, or trihalomethyl; $R^3$ is hydrogen or alkyl; and $R^4$ is H except when $R^3$ is alkyl then $R^4$ may be alkyl; $R^5$, $R^6$, and $R^8$ and $R^9$ are independently halogen, hydrogen, hydroxy, alkyl or alkoxy; and $R^7$ is hydrogen or alkyl; which is free of 6-trans isomers.

2. A compound of claim 1 which is

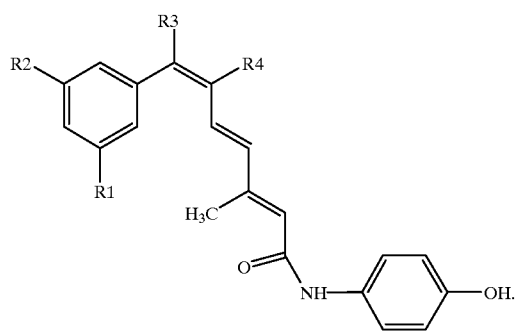

Formula 2

3. A compound of claim 1 wherein $R^3$ is methyl and $R^4$ is hydrogen.
4. A compound of claim 1 wherein $R^1$ and $R^2$ are hydrogen.
5. A compound of claim 1 wherein $R^1$ and $R^2$ are halogen.
6. A compound of claim 5 wherein $R^1$ and $R^2$ are bromine.
7. A compound of claim 1 wherein $R^1$ and $R^2$ are alkyl.
8. A compound of claim 7 wherein $R^1$ and $R^2$ are methyl.
9. A compound of claim 1 wherein $R^1$ and $R^2$ are alkoxy.
10. A compound of claim 9 wherein $R^1$ and $R^2$ are methoxy.
11. A compound of claim 1 wherein $R^1$ and $R^2$ are trihalomethyl.
12. A compound of claim 1 wherein $R^1$ and $R^2$ are trifluoromethyl.
13. A compound of claim 2 wherein $R^3$ is methyl and $R^4$ is hydrogen.
14. A compound of claim 2 wherein $R^3$ and $R^4$ are hydrogen.
15. A compound of claim 2 wherein $R^3$ and $R^4$ are methyl.
16. A compound of claim 13 wherein $R^1$ and $R^2$ are trifluoromethyl which is N-(4-hydroxyphenyl)-(2E,4E,6Z)-7-[3,5-bis(trifluoromethyl)phenyl]-3, 7-dimethyl-2,4,6-heptatrienamide.
17. A compound of claim 14 wherein $R^1$ and $R^2$ are trifluoromethyl which is N-(4-hydroxyphenyl)-(2E,4E,6Z)-7-[3,5-bis(trifluoromethyl)phenyl]-3-methyl-2,4,6-heptatrienamide.
18. A compound of claim 15 wherein $R^1$ and $R^2$ are trifluoromethyl which is N-(4-hydroxyphenyl)-(2E,4E,6Z)-7-[3,5-bis(trifluoromethyl)phenyl]-3, 6, 7-trimethyl-2,4,6-heptatrienamide.
19. A compound of claim 13 wherein $R^1$ and $R^2$ are bromine which is N-(4-hydroxyphenyl)-(2E,4E,6Z)-7-[3,5-bis(bromo)phenyl]-3, 7-dimethyl-2,4,6-heptatrienamide.
20. A compound of claim 14 wherein $R^1$ and $R^2$ are bromine.
21. A compound of claim 15 wherein $R^1$ and $R^2$ are bromine.
22. A compound of claim 13 wherein $R^1$ and $R^2$ are methyl which is N-(4-hydroxyphenyl)-(2E,4E,6Z)-7-[3,5-bis(methyl)phenyl]-3, 7-dimethyl-2,4,6-heptatrienamide.
23. A compound of claim 14 wherein $R^1$ and $R^2$ are methyl.
24. A compound of claim 15 wherein $R^1$ and $R^2$ are methyl.
25. A compound of claim 13 wherein $R^1$ and $R^2$ are methoxy which is N-(4-hydroxyphenyl)-(2E,4E,6Z)-7-[3,5-bis(methoxy)phenyl] -3, 7-dimethyl-2,4,6-heptatrienamide.
26. A compound of claim 14 wherein $R^1$ and R2 are methoxy.
27. A compound of claim 15 wherein $R^1$ and $R^2$ are methoxy.
28. A compound of claim 13 wherein $R^1$ and $R^2$ are hydrogen which is N-(4-hydroxyphenyl)-(2E,4E,6Z)-7-[phenyl]-3,7-dimethyl-2,4,6-heptatrienamide.
29. A compound of claim 14 wherein $R^1$ and $R^2$ are hydrogen.
30. A compound of claim 15 wherein $R^1$ and $R^2$ are hydrogen.
31. A pharmaceutical composition which comprises the compound of claim 1 and a pharmaceutically acceptable carrier.
32. A method for treating breast cancer which comprises providing to an individual with breast carcinoma an amount of the compound of claim 1 effective to inhibit growth of the carcinoma cells.

* * * * *